United States Patent [19]

Dybas et al.

[11] Patent Number: 5,710,259
[45] Date of Patent: Jan. 20, 1998

[54] OLIGOSACCHARIDE-CONTAINING 14-AMINOSTEROID COMPOUNDS AND NOVEL DIASTEREOSELECTIVE AMINOSTEROID PROCESS CHEMISTRY

[75] Inventors: Paul Michael Dybas, Port Crane; Roland Norman Johnson, Norwich; Randy Stuart Muth, Poolville; Song Liu, Norwich, all of N.Y.

[73] Assignee: The Procter & Gamble Company, Cincinnati, Ohio

[21] Appl. No.: 459,911

[22] Filed: Jun. 2, 1995

Related U.S. Application Data

[62] Division of Ser. No. 406,833, Mar. 20, 1995, abandoned, which is a continuation of Ser. No. 126,459, Sep. 24, 1993, abandoned.

[51] Int. Cl.$^6$ .......................... C07H 15/24; A61K 31/705
[52] U.S. Cl. .......................... 536/18.5; 536/17.9; 536/5; 514/26
[58] Field of Search .................... 514/26; 536/5, 536/17.9, 18.5

[56] References Cited

U.S. PATENT DOCUMENTS

| | | | |
|---|---|---|---|
| 3,567,712 | 3/1971 | Ruggieri et al. | 260/239.5 |
| 4,552,868 | 11/1985 | Jarreau et al. | 514/26 |
| 4,584,289 | 4/1986 | Jarreau et al. | 514/182 |
| 4,885,280 | 12/1989 | Jarreau et al. | 514/26 |

*Primary Examiner*—John Kight
*Assistant Examiner*—Howard C. Lee
*Attorney, Agent, or Firm*—Mary P. McMahon; Karen F. Clark; Jacobus C. Rasser

[57] ABSTRACT

The present invention relates to oligosaccharide-containing 14-aminosteroid compounds and the pharmaceutically-acceptable acid salts or esters thereof of the general formula:

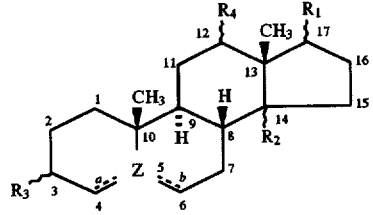

wherein
a) $R_1$ is
 (i) $COOR_5$, where
  $R_5$ is hydrogen, a 1-6 carbon lower alkyl; a 1-6 carbon lower alkyl substituted by an amino group; an arylalkyl or heteroarylalkyl or a carbocyclic ring, or
 (ii) $CHR_6OH$, where
  $R_6$ is a hydrogen atom or 1-6 carbon lower alkyl group, or
 (iii) $COR'''$, where $R'''$ is hydrogen; 1-6 carbon lower alkyl; 1-6 carbon lower alkyl substituted amino; amino or dialkylamino; and
b) $R_2$ is $-NR_7R_8$, where
 $R_7$ and $R_8$, which may be the same or different, are hydrogen atoms or a 1-6 carbon lower alkyl; and
c) $R_3$ is an oligosaccharide sugar residue; and
d) $R_4$ is
 (i) OH, or
 (ii) H, or
 (iii) $OR_{13}$, where
  $R_{13}$ is a monosaccharide sugar residue; acetoxy; benzoxy; arylalkyl or heteroarylalkyl; and
e) Z is
 (i) —CH—, where
  a and b are single bonds, or
 (ii) =C, where
  either a or b is a double bond.

The present invention also relates to a process for introducing an amino group at the 14-position on a steroid nucleus wherein said amino group is diastereoselectively introduced onto the 14-position of the steroid nucleus via an iodoisocyanate addition comprising the steps of:

a) adding the iodoisocyanate to the 14-15 position double bond on the steroid nucleus; and
b) dehalogenation; and
c) isocyanate conversion to the amine moiety on the 14-position of the steroid nucleus.

12 Claims, No Drawings

OLIGOSACCHARIDE-CONTAINING 14-AMINOSTEROID COMPOUNDS AND NOVEL DIASTEREOSELECTIVE AMINOSTEROID PROCESS CHEMISTRY

This is a division of application Ser. No. 08/406,833, filed on Mar. 20, 1995, now abandoned, which is a continuation of application Ser. No. 08/126,459, filed on Sep. 24, 1993, now abandoned.

BACKGROUND OF THE INVENTION

This invention relates to novel oligosaccharide-containing 14-aminosteroid compounds. This invention also relates to pharmaceutical compositions containing these novel compounds as well as to a method of treating Congestive Heart Failure (CHF) using the compounds of the present invention. This invention further relates to a novel process for introducing an amino group at the 14-position on the steroid nucleus.

CHF is a progressive disease wherein the heart is increasingly unable to supply adequate cardiac output (CO), which is the volume of blood pumped by the heart over time, to deliver the oxygenated blood to the peripheral tissues. When the heart initially fails, the rest of the body compensates for the loss in CO and such compensatory mechanisms eventually result in the syndrome known as CHF. As CHF progresses, structural and hemodynamic damages occur. Such structural damage manifests itself macroscopically as ventricular hypertrophy in the myocardium, and microscopically as interstitial, perivascular and replacement fibrosis in the ventricle wall, decreased myocardial capillary density, and myocardial cell death. When fibrosis of the myocardial tissue occurs it compromises the functioning of the heart because the remaining viable myocardial cells have a greater workload.

Hemodynamically, in the failing heart, the capacity to develop force during systole (the phase in the cardiac cycle during which ejection of blood from the ventricles occurs) is reduced. Thus, a greater end-diastolic volume (during the diastolic phase of the cardiac cycle filling of the ventricles occurs) is needed to perform any given level of external work. In cardiac failure, reduced ejection, caused by a mismatch of work capacity and load, results in an increase in end diastolic pressure and pulmonary capillary pressure. Pulmonary congestion and peripheral edema often follow. From the patient's perspective, as CHF progresses, the patient experiences increasingly worsening symptoms of fatigue and dyspnea.

Effective treatment of CHF requires a determination of its etiology, if possible, because some CHF etiologies have their own unique form of treatment. CHF has a variety of etiologies, including diseases of the myocardium such as coronary artery disease or myocarditis; diseases of the valves, such as mitral valve prolapse or aortic stenosis; pericardial diseases; congenital heart disease; pulmonary disease, cardiac arrhythmias, hypertension, and diabetes. For example, if the etiology of CHF is myocarditis or an arrhythmia, then treating the patient with an antimicrobial or an antiarrhythmic agent, respectively, may restore the patient to normal cardiac function.

However, once the etiologies not responding to other treatments have been ruled out, treatment by one or more of three modalities is initiated: 1) improvement of the heart's pumping capacity by administration of an inotropic agent, such as digitalis, 2) reduction of the heart's workload by rest and/or by administration of vasodilators such as captopril, and 3) controlling sodium and water retention by a low sodium diet or administration of a diuretic such as thiazide. Treatment of CHF is individualized according to the patients symptomatology and tolerance for certain medications. For example, some patients may have a strong tendency to develop digitalis toxicity, while other patients with mild symptoms may benefit from diuretics which have a greater therapeutic index. Moreover, current wisdom suggests that diuretics are appropriate first line CHF therapy and that diuretic treatment should be followed by vasodilators and digitalis. It has also been noted that digitalis is most effective in patients suffering from severe CHF. See generally, Braunwald, *Heart Disease: A Textbook of Cardiovascular Medicine*, Vol. (3rd ed. 1988), Chung, E. K., *Quick Reference to Cardiovascular Disease*, Chapter 27 (2d ed. 1983) and Fowler, N. O., *Cardiac Diagnosis and Treatment*, Chapter 12 (2d ed. 1976).

While digitalis is useful for ameliorating the symptoms associated with the hemodynamic problems characteristic of severe CHF, its low therapeutic index, in effect, limits its therapeutic utility. See generally, Braunwald, *Heart Disease: A Textbook of Cardiovascular Medicine*, Vol. (3rd ed. 1988), Chung, E. K., *Quick Reference to Cardiovascular Disease*, Chapter 27 (2d ed. 1983) and Fowler, N. O., *Cardiac Diagnosis and Treatment*, Chapter 12 (2d ed. 1976) and Goodman and Gilman, *The Pharmacological Basis of Therapeutics*, Chapter 34 (8th ed., 1990).

The toxicity problems associated with digitalis have prompted investigators to attempt to develop safer cardioactive compounds. Cardioactive steroid nucleus containing compounds have been described in the following patents: World Patent Publication WO 87/04167 to Chiodini, et al. published Jul. 16, 1987 describes aminoglycoside steroid derivatives substituted by an amino-sugar residue at the 3-position and an acetal linkage at the 14-position. The disclosure states that the compounds are useful for the treatment of hypertension. French Patent 2,642,973 of Guina published Aug. 17, 1990 describes a digitalis-like compound, 2,3-dioxymethyl-6-methyl-3-beta-D-glucose-strophanthidine, which contains the steroid nucleus substituted at the 3-position with a glucose moiety and at the 17-position with the lactone moiety, and at the 14-position with a hydroxyl group. The disclosure states that the compound is useful in preventing pathologic states resulting from cardiac insufficiencies for which digitalis is prescribed and for preventing pathologic states resulting from hypertension due to arterial calcification. The Guina compound is also alleged to be a positive inotrope, a peripheral vasodilator, and an anti-arrhythmic agent. World Patent Publication WO 87/04168 to Chiodini et al., Jul. 16, 1987 discloses an aminoglycoside steroid having an alkyl substituted amino sugar at the 3-position, such as 2-amino or 2-alkylamino-2-deoxyhexopyranosyl, 3-amino or 3-alkylamino-3-deoxy-hexo-pyranosyl, 3-amino or 3-alkylamino-3,6-dideoxy-hexopyranosyl, 3 amino or 3-alkylamino-2,3,6-trideoxy-hexopyranosy 4-amino or 4-alkylamino 2,4,6-trideoxy-hexopyranosyl residues, and a cyclic amide (lactam) at the 17-position. The 14-position is substituted with a H. The compound is said to be useful as an antihypertensive. World Patent Publication WO 91/17176 to Kenny, et al., published Nov. 14, 1991 discloses asteroid glycoside, useful as a pressor agent, having a sugar moiety at the 3-position; such as a pentose, hexose or combinations thereof, and a lactone ring at the 17-position, the 14-position is substituted with an OH, H or a F, Cl, Br or $NH_2$; DD 296,502 A5 granted Dec. 5, 1991 discloses asteroid amide for treating cardial insufficiency wherein the 3-position is substituted with a sulphonyl amino group and the 17-position is substituted with a 5 or 6-membered lactone ring; the 14-position is substituted with an OH. U.S. Pat. No. 5,144,017 to LaBella, Sep. 1, 1992 discloses steroid compounds said to be useful as cardiac stimulants wherein the 3-position is substituted with a glycoside radical such as β-D-glucoside, α-L-rhamnoside, tridigitoxoside and the 17-position is substituted with an acetoxy group or an amino group; and the 14-position has an OH group; and U.S. Pat. No. 5,175,281 to McCall, Dec. 29, 1992 discloses pyrimidinylpiperazinyl steroid compounds useful in treating spinal trauma, head injury and the subsequent cerebral vasospasm, preventing damage following cardiopulmonary resuscitation and cardiac infarction wherein the 3-position is OH, CH$_3$O, COOH, or benzoxy, the 14-position is a H and the 17-position is a heterocyclic amine. DD 256,134 A1 to Wunderwald, et al., granted Apr. 27, 1988 discloses a process for making cardioactive steroids wherein the 3-position of the steroid molecule is substituted with a morpholinoformyloxy residue, and the 17-position of the steroid nucleus is substituted with a lactone ring; and the 14-position is substituted with OH, H or an olefin. Said compounds are alleged to be useful for increasing cardiac contractility. JP 4-290899 to Ichikawa, et al., laid open Oct. 15, 1992, discloses a cardiotonic steroid compound wherein the 3-position of the steroid nucleus is substituted with an oligosaccharide; wherein further said oligosaccharide consists of three glucopyranosyl moieties and the 14-position is substituted with an OH group, and the 17-position is substituted with a lactone ring. Templeton, et al., 36 *J. Med. Chem.* 42–45 (1993) disclose the synthesis of derivatives of 14-hydroxy-21-nor-5β, 14β-pregnane and 5β, 14β-pregnane C-3 α-L-rhamnosides and tris-β-D-digitoxosides. Said compounds are reported to be effective cardiotonics. These derivatives, possessing a C-17β COCH$_2$OH, CH$_2$OH, CO$_2$H, CO$_2$Me, CH$_2$NH$_2$, or CH$_2$NO$_2$ group, bind to the digitalis receptor recognition site of heart muscle. Templeton, et al., 1 *J. Chem. Sci. Perkin. Trans.*, 2503–2517 (1992) disclose the synthesis of 20α- and 20β-acetamido-, amino-, nitro- and hydroxy-3β-glycoside (α-L-rhamnopyranoside and tris-β-D-digitoxoside) and genin derivatives of 14-hydroxy-5β, 14β-pregnane together with the C-20 oxime, hydrazone and amidinohydrazone. These compounds are asserted to be effective cardiotonics.

Additionally, angiotensin converting enzyme inhibitors (ACEI) have been shown to reduce mortality in CHF patients. See Nicklas, J. M. and Pitt, B., et al. (The SOLVD Investigators), "Effect of Enalapril on Survival in Patients with Reduced Left Ventricular Ejection Fractions and Congestive Heart Failure", *N. Engl. J. Med.* 325(5):293 (1991).

Nevertheless, four million people still suffer from CHF, The five year mortality after diagnosis of CHF is 60% for men and 45% for women. This is a clear indication that better therapies directed toward treating CHF are needed. See Parmley, W. W., "Pathophysiology and Current Therapy of Congestive Heart Failure", *J. Am. Col. Cardiol.* 13:771–785 (1989); Francis, G. S. et al., "Congestive Heart Failure: Pathophysiology and Therapy," *Cardiovascular Pharmacology*, 3rd Edition (1990).

The 14-aminosteroid compounds have been shown to be useful in treating CHF by increasing cardiac contractility. These compounds provide the therapeutic benefit of increased cardiac contractility without the side effects of digitalis. These 14-aminosteroids and methods for their preparation are described in the following three patents, all incorporated by reference herein: U.S. Pat. No. 4,325,879, Jarreau, et al. issued Apr. 20, 1982 (U.S. Pat. No. '879) (equivalent to French Patent Application 2,464,270); U.S. Pat. No. 4,552,868, Jarreau, et al., issued Nov. 12, 1985 (U.S. Pat. No. '868); U.S. Pat. No. 4,584,289, Jarreau, et al., issued Apr. 22, 1986 (U.S. Pat. No. '289) and U.S. Pat. No. 4,885,280, Jarreau, et al., issued Dec. 5, 1989 (U.S. Pat. No. '280). These four patents describe 14-aminosteroid compounds possessing cardiotonic activity and processes for their preparation. U.S. Pat. Nos. '879; '868; '289 and '280 all disclose the use of hydrazoic acid to form an azide derivative at the 14-position which is then reduced to the amino group. Adeoti, S. B., et al., "Introduction Of A 14β-Nitrated Function Into The Steroid Ring To Prepare The Cardioactive Rolecule, 14β-Amino-5β-Pregnane-3β,20β-Diol, From Progesterone and Deoxycholic Acid," 45(12) *Tetrahedron Letters*, 3717–3730 (1989) disclose two methods for introducing a 14β-amino function into asteroid molecule, involving 1) a cyclisation reaction in the presence of N$_3$H, BF$_3$.Et$_2$O or ammonia or 2) treating asteroid nucleus with N$_3$H, Bf$_3$.Et$_2$O . Said methods allow for the preparation of the cardioactive 14β-amino-5β-pregnane-3β, 20β diol. Naidoo, B. K., et al., "Cardiotonic Steroids I: Importance of 14β-hydroxy Group in Digitoxigenin," 63 (9) *Jnl Pharm Sci.*, 1391–1394 (1974) disclose an experimental attempt to prepare a 14β-amino steroid compound using iodoisocyanate. However, the investigators were not successful in introducing the amino group on the 14-position of the steroid nucleus utilizing the iodoisocyanate chemistry. The applicability of the iodoisocyanate chemistry to the synthesis of steroid compounds is generally disclosed in, Ponsold, K., et al., "Gekoppelt Additionsreaktionen an 14, 15-ungesattigten Androstanen Einfluß des positiven Halogens auf die Regioselektivitat," *Journal f. prakt. Chemie*, Band 325, Heft 1, 1983, S. 123–132; Ponsold, K., et al. "Synthese und Reaktivitat von Estra-1,3, 5(10)-trienen mit heterocyclischen Vierringen in 14,15-Stellung", *Journal f. prakt. Chemie*, Band 328, Heft 5/6, 1986, S.673–681; and Bohl. M., et al", "Quantitative structure-activity relationships of estrogenic steroids substituted at C14, C15", *Steroid Biochem.* Vol. 26 No. 5, pp. 589–597 1987.

It has now been discovered that the 14-aminosteroid compounds of the present invention wherein the 3-position is substituted with an oligosaccharide moiety are more effective inotropes. Said oligosaccharide-containing 14-aminosteroids are more resistant to metabolism and therefore provide a longer duration of inotropic activity than the prior art 14-aminosteroids. It has also been discovered that the amino group can be introduced at the 14-position on the steroid nucleus by a process utilizing iodoisocyanate chemistry which is safer and more efficient than the prior art processes.

SUMMARY OF THE INVENTION

Oligosaccharide-containing 14-aminosteroid compounds and the pharmaceutically-acceptable acid salts or esters thereof of the general formula:

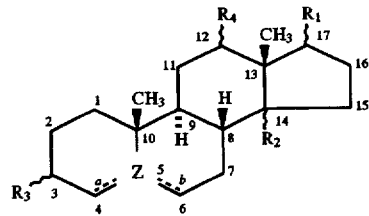

wherein a) $R_1$ is
  (i) $COOR_5$, where
    $R_5$ is hydrogen; a 1–6 carbon alkyl; a 1–6 carbon lower alkyl substituted by an amino group; an arylalkyl or heteroarylalkyl or a carbocyclic ring; or
  (ii) $CHR_6OH$, where
    $R_6$ is a hydrogen atom or a 1–6 carbon lower alkyl; or
  (iii) $COR'''$, where
    $R'''$ is hydrogen; 1–6 carbon lower alkyl; 1–6 carbon lower alkyl substituted amino; amino or dialkylamino; and b) $R_2$ is $-NR_7R_8$, where
  $R_7$ and $R_8$, which may be the same or different, are hydrogen atoms or a 1–6 carbon lower alkyl group; and c) $R_3$ is
  (i) an oligosaccharide sugar residue having the following structure:

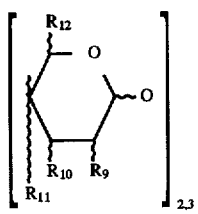

where
  $R_9$ is hydrogen; methyl; hydroxy; carboxy; acetoxy; arylalkyloxy; heteroarylalkyloxy; or benzoxy; $R_{10}$ is hydrogen; methyl; carboxy; acetoxy; arylalkyloxy; heteroarylalkyloxy; benzoxy or hydroxy; $R_{11}$ is oxygen; wherein further when $R_{11}$ is a substituent on the terminal monosaccharide sugar residue; $R_{11}$ is OH; methyl; acetoxy; heteroarylalkyloxy; arylalkyloxy; and $R_{12}$ is a hydrogen; methyl; methylhydroxymethyl; or acetoxymethyl; or (ii) an oligosaccharide sugar residue having the following structure:

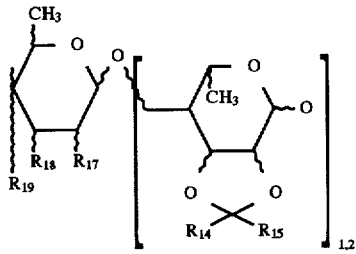

where
  $R_{14}$ and $R_{15}$, which may be the same or different, are hydrogen; 1–6 carbon lower alkyl; arylalkyl; heteroaryl alkyl; heteroaryl or aryl; $R_{17}$ can be hydrogen; hydroxy; acetoxy or benzoxy; $R_{18}$ and $R_{19}$ are hydroxy; acetoxy and benzoxy; or (iii) an oligosaccharide residue having the following structure:

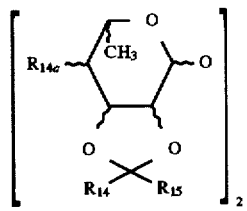

where
  $R_{14}$ and $R_{15}$, which may be the same or different, are hydrogen; 1–6 carbon lower alkyl; heteroarylalkyl; arylalkyl or aryl; $R_{14a}$ is oxygen; wherein further when $R_{14a}$ is a substituent on the terminal monosaccharide residue; $R_{14a}$ must be hydroxy; methyl; acetoxy; arylalkyloxy or heteroarylalkyloxy; and d) $R_4$ is
  (i) OH, or
  (ii) H, or
  (iii) $OR_{13}$, where
    $R_{13}$ is a monosaccharide sugar residue; acetoxy; benzoxy; arylalkyl or heteroarylalkyl; and e) Z is
  (i) —CH—, where
    a and b are single bonds, or
  (ii) =C, where
    either a or b is a double bond.

The present invention also encompasses a process for introducing an amino group at the 14-position on the steroid nucleus, wherein said amino group is diasteroselectively introduced onto the 14-position of the steroid nucleus via an iodoisocyanate addition comprising the steps of:

a) adding the iodoisocyanate to the 14–15 position double bond on the steroid nucleus; and b) dehalogenation; and c) isocyanate conversion to the amine moiety on the 14-position of the steroid nucleus.

DEFINITIONS AND USAGE OF TERMS

The following is a list of definitions for terms used herein.

"Aminosteroid" is asteroid ring compound having an amino group on the steroid nucleus.

"Alkyl" is an unsubstituted or substituted, straight-chain, cyclic or branched, saturated hydrocarbon chain having 1 to 8 carbon atoms, and preferably, unless otherwise stated, from 1 to 4 carbon atoms. Preferred alkyl groups include, but are not limited to, methyl, ethyl, propyl, isopropyl, and butyl; a monovalent radical derived from an aliphatic hydrocarbon by removal of 1 H; as methyl. A lower alkyl group contains 1–6 carbon atoms.

"Heteroalkyl" as used herein is an unsubstituted or substituted, saturated chain having from 3 to 8-members and comprising carbon atoms and one or two heteroatoms.

"Alkenyl" is an unsubstituted or substituted, straight-chain or branched, hydrocarbon chain having from 2 to 8 carbon atoms, preferably from 2 to 4 carbon atoms, and having at least one olefinic double bond.

"Alkynyl" is an unsubstituted or substituted, straight-chain or branched, hydrocarbon chain having from 2 to 8 carbon atoms, preferably from 2 to 4 carbon atoms, and having at least one triple bond.

"Acetate": A salt of acetic acid containing the $CH_3COO-$ radical.

"Acetoxy": Acetyloxy. The radical CH₃COO—.

"Acetyl": The acyl radical CH₃CO—.

"Aglycone": That component of a glycoside, e.g., plant pigment, which is not a sugar.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms.

"Heterocyclic ring" or "Heterocycle" as used herein is an unsubstituted or substituted, saturated or unsaturated or aromatic ring comprised of carbon atoms and one or more heteroatoms in the ring. Heterocyclic rings generally contain from 3 to 8, preferably 5 to 7, atoms. Unless otherwise stated, the heteroatom may be independently chosen from nitrogen, sulfur, and oxygen.

"Aryl" is an aromatic carbocyclic ring. Aryl groups include, but are not limited to, phenyl, tolyl, xylyl, cumenyl, and naphthyl; an organic radical derived from an aromatic hydrocarbon by the removal of one atom; e.g. phenyl from benzene.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g. —O-alkyl or —O-alkenyl); "Alkoxy" An alkyl radical attached to the remainder of the molecule by oxygen; as, methoxy. Preferred alkoxy groups include, but are not limited to, methoxy, ethoxy, propoxy, and alkyloxy.

"Hydroxylalkyl" is a substituted hydrocarbon chain which has a hydroxy substituent (e.g. —OH), and may have other substituents. Preferred hydroxyalkyl groups include, but are not limited to, hydroxyethyl, hydroxypropyl, phenylhydroxalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain, (e.g. alkyl) substituted with an amine moiety (e.g. NH-alkyl-), such as dimethylamino alkyl.

"Alkylamino" is an amino moiety having one or two alkyl substituents (e.g. —N-alkyl).

"Alkenylamino" is an amino moiety having one or two alkenyl substituents (e.g. —N-alkenyl).

"Alkynylamino" is an amino moiety having one or two alkynyl substituents (e.g. —N-alkynyl).

"Alkylimino" is an imino moiety having one or two alkyl substituents (e.g. N=alkyl-).

"Arylalkyloxy" is an oxygen atom having an aryl alkyl substituent, e.g. phenoxymethyl; phenylmethyleneoxy.

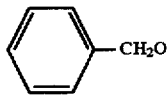

"Heteroarylalkyloxy" is an oxygen atom having a heteroarylalkyl substituent, e.g.

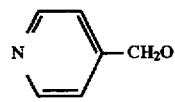

"Arylalkyl" is an alkyl moiety substituted with an aryl group. Preferred arylalkyl groups include benzyl and phenylethyl.

"Heteroarylalkyl" is an alkyl moiety substituted with a heteroaryl group.

"Arylamino" is an amino moiety substituted with an aryl group (e.g. —NH-aryl).

"Aryloxy" is an oxygen atom having an aryl substituent (e.g. —O-aryl).

"Acyl" or "carbonyl" is a moiety formed by removal of the hydroxy from a carboxylic acid (e.g. R—C(=O)—). Preferred alkylacyl groups include, but are not limited to, acetyl, propionyl, and butanoyl. "Acyloxy" is an oxygen atom having an acyl substituent (e.g. —O-acyl); for example, —O—C(=O)-alkyl.

"Acylamino" is an amino moiety having an acyl substituent (e.g. —N-acyl); for example, —NH—(C=O)-alkyl.

"Benzoxy": The benzoyloxy radical.

"Benzoyl": The aryl radical, C₆H₅CO—, derived from benzoic acid.

"Benzoyloxy": Benzoxy. The radical C₆H₅COO—, derived from benzoic acid.

"Carbamate": A salt of carbamic acid; it contains the —NCO₂— radical, also known in the art as urethane or carbamic ester.

"Carboxy": Prefix indicating the acidic carboxyl group.

"Ester": An organic salt formed from an alcohol (base) and an organic acid by elimination of water; functional group derivatives of carboxylic acids are those compounds that are transformed into carboxylic acids by simple hydrolysis. The most common such derivatives are esters in which the hydroxy group is replaced by an alkoxy group, e.g.

"Glycoside": A natural compound of a sugar with another substance, which hydrolyzes a sugar plus a principle: (e.g. coniferin yields glucose plus coniferyl alcohol as the principle; glucosides yield glucose, fructosides yield fructose, galactoside yield galactose, etc; the cyclic acetal of a carbohydrate.

"Halo", "halogen", or "halide" is a chloro, bromo, fluoro, or iodo atom radical. Chloro, bromo, and fluoro are preferred halides.

"Lactone": Any of a class of inner esters of hydroxy carboxylic acids formed by the loss of a molecule of water from the hydroxy and carboxyl groups of the acids, characterized by the carbonyl-oxy grouping —OCO— in a ring and classed according to the position of the hydroxy group in the parent acid; cyclic ester.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halides (such as chloride) salts.

"Salts": Substances produced from the reaction between acids and bases; a compound of a metal (positive) and nonmetal (negative) radical: M·OH (base)+HX (acid)=MX (salt)+H₂O (water).

"Steroid nucleus": Generic name for a family of lipid compounds comprising the sterols, bile acids, cardiac glycosides, saponins, and sex hormones.

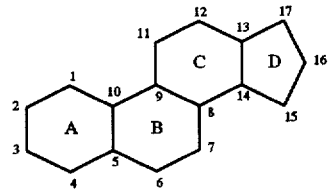

"Substituent": Any atom or group replacing the hydrogen of a parent compound.

"Substitute": To replace one element or radical in a compound by a substituent.

"Substituted": Pertaining to a compound which has undergone substitution.

"Substitution": A reaction in which an atom or group of atoms in a (usually organic) molecule is exchanged for another.

Substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

A "monosaccharide" is a single sugar moiety; e.g. hexose, 2-deoxyglucose, 6-deoxyhexose, 2,6-dideoxyhexose, etc., rhamnose, glucose, arabinose, digitoxose, fructose, galactose; rhamnopyrannose, hexopyrranose, 6-deoxyglucose, 4,6-dideoxyglycopyranose, mannose, cymarose, xylose, lyxose, ribose, digitalose, 4-amino-2,4,6-trideoxylyxohexopyranose, 4-amino 4,6, dideoxyglucopyranose, 2,3-dideoxyrhamnopyranose, 4-methoxy 4,6-dideoxy rhamnopyranose.

An "oligosaccharide" is a sugar having 2–8 monosaccharide sugar residues, preferably 2–3. The last monosaccharide residue of the oligosaccharide is known as the "terminal" monosaccharide residue. The monosaccharide residues comprising the oligosaccharide may be the same or different. Said monosaccharide residues are joined by a glycosidic linkage from the OH group of one monosaccharide residue to the anomeric carbon of the other monosaccharide residue.

The "monosaccharide" or "oligosaccharide" residue can be graphically depicted in either a ring or a chair configuration. For example, glucose (a monosaccharide) can be represented accordingly:

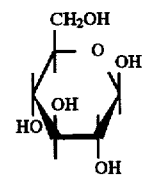

"ring"

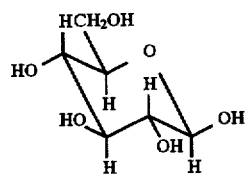

"chair"

DETAILED DESCRIPTION OF THE INVENTION

The present invention encompasses certain oligosaccharide-containing 14-aminosteroid compounds, methods for their manufacture, pharmaceutical compositions thereof, and a method of treatment utilizing said novel compounds and compositions thereof for treating congestive heart failure in humans or other mammals. Specific compounds and compositions to be used in the invention must, accordingly, be pharmaceutically-acceptable. As used herein, such a "pharmaceutically-acceptable" component is one that is suitable for use with humans and/or other mammals without undue adverse side effects (such as toxicity, irritation, and allergic response), commensurate with a reasonable benefit/risk ratio.

Active Materials

Oligosaccharide-containing 14-aminosteroid compounds and the pharmaceutically-acceptable acid salts or esters thereof of the general formula:

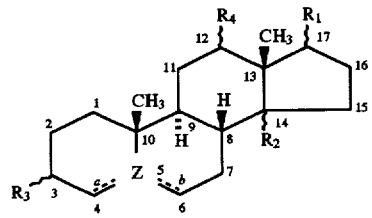

wherein a) $R_1$ is
  (i) $COOR_5$, where
    $R_5$ is hydrogen; a 1–6 carbon lower alkyl; a 1–6 carbon lower alkyl substituted by an amino group; an arylalkyl or heteroarylalkyl or a carbocyclic ring, or
  (ii) $CHR_6OH$, where
    $R_6$ is a hydrogen atom or a 1–6 carbon lower alkyl, or
  (iii) $COR'''$, where
    $R'''$ is hydrogen; 1–6 carbon lower alkyl; 1–6 carbon lower alkyl substituted amino; amino or dialkylamino; and b) $R_2$ is $—NR_7R_8$, where
  $R_7$ and $R_8$, which may be the same or different, are hydrogen atoms or a 1–6 carbon lower alkyl group; and c) $R_3$ is
  (i) an oligosaccharide sugar residue having the following structure:

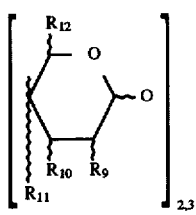

where
  $R_9$ is hydrogen; methyl; hydroxy; carboxy; acetoxy; arylalkyloxy; heteroarylalkyloxy or benzoxy; $R_{10}$ is hydrogen; methyl; carboxy; acetoxy; arylalkyloxy; heteroarylalkyloxy; benzoxy or hydroxy; $R_{11}$ is oxygen; wherein further when $R_{11}$ is a substituent on the terminal monosaccharide sugar residue; $R_{11}$ is OH; methyl; acetoxy; heteroarylalkyloxy; arylalkyloxy; and $R_{12}$ is a hydrogen; methyl; methylhydroxymethyl; or acetoxymethyl; or (ii) an oligosaccharide sugar residue having the following structure:

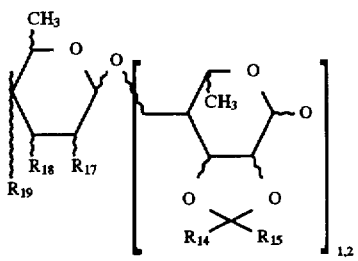

where
  $R_{14}$ and $R_{15}$, which may be the same or different, are hydrogen; 1–6 carbon lower alkyl; arylalkyl heteroarylalkyl; heteroaryl or aryl; $R_{17}$ can be hydrogen; hydroxy; acetoxy or benzoxy; $R_{18}$ and $R_{19}$ are hydroxy; acetoxy and benzoxy; or (iii) an oligosaccharide residue having the following structure:

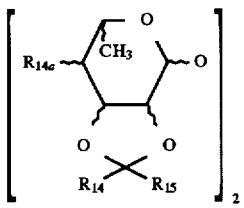

where
  $R_{14}$ and $R_{15}$, which may be the same or different, are hydrogen; 1–6 carbon lower alkyl; heteroaryl alkyl; aryl alkyl; aryl or heteroaryl; $R_{14a}$ is oxygen; wherein further when $R_{14a}$ is a substituent on the terminal monosaccharide sugar residue, $R_{14a}$ must be hydroxy; methyl; acetoxy; arylalkyloxy or heteroarylalkyloxy; and d) $R_4$ is
  (i) OH, or
  (ii) H, or
  (iii) $OR_{13}$, where
    $R_{13}$ is a monosaccharide sugar residue; acetoxy; benzoxy; aryl alkyl or heteroarylalkyl; and e) Z is
  (i) —CH—, where
    a and b are single bonds, or
  (ii) =C, where
    either a or b is a double bond.

The "~" symbol, as used herein, indicates that the stereochemistry is undefined, and that the substituents on the steroid nucleus can be in either the α or β configuration. Preferably, the substituents on the steroid nucleus are in the β-configuration. Further, the monosaccharide units comprising the oligosaccharide residue can be in either the α or β configuration. One skilled in the art of carbohydrate chemistry understands that the configuration of the substituents on a given sugar residue is defined by the specific named sugar.

The present invention also encompasses a process for introducing an amino group at the 14-position on the steroid nucleus wherein the amino group is diasteroselectively introduced onto the 14-position of the steroid nucleus via an iodoisocyanate addition comprising the steps of:

a) adding the iodoisocyanate to the 14–15 position double bond on the steroid nucleus; and b) dehalogenation; and c) isocyanate conversion to the amine moiety on the 14-position of the steroid nucleus.

THE OLIGOSACCHARIDE-CONTAINING 14-AMINO STEROID COMPOUNDS OF THE PRESENT INVENTION

The Steroid Nucleus

The novel oligosaccharide-containing 14-aminosteroid compounds of the present invention are comprised of a steroid nucleus wherein said steroid nucleus is variously substituted.

The Substituents on the Steroid Nucleus

The $R_1$ Substituents

The $R_1$ substituent is at the 17-position on the steroid nucleus. There are three (3) possible $R_1$ substituents. $R_1$ can be a carboxylic acid ester, $COOR_5$, where $R_5$ is hydrogen, a 1–6 carbon lower alkyl group, a 1–6 carbon lower alkyl group substituted by an amino group, an arylalkyl group or heteroarylalkyl group or a carbocyclic ring. Preferred $R_5$ substituents are 1–6 carbon lower alkyl, arylalkyl or a carbocycle, the more preferred $R_5$ is a 1–6 carbon lower alkyl and the most preferred $R_5$ is methyl; thus, $R_1$ is $COOCH_3$ (carboxymethylester).

$R_1$ can also be $CHR_6OH$ where $R_6$ is a hydrogen atom or lower alkyl group containing 1 to 6 carbon atoms; the preferred $R_6$ is H or $CH_3$; thus, $R_1$ is $CH_2OH$ or $CH(CH_3)OH$.

Finally, $R_1$ can be COR''', where R''' is hydrogen, 1–6 carbon lower alkyl, methylamino, amino or dialkylamino. The preferred R''' is amino or methylamino. The most preferred R''' is amino; thus, $R_1$ is $CONH_2$.

The most preferred $R_1$ substituent on the steroid nucleus is the carboxylic acid ester, $COOR_5$, where $R_5$ is methyl ($COOCH_3$).

The $R_2$ Substituent

The $R_2$ substituent is at the 14-position on the steroid nucleus. There is one (1) $R_2$ substituent. $R_2$ is $-NR_7R_8$ where $R_7$ and $R_8$, which may be the same or different, are hydrogen atoms or lower alkyl group containing 1 to 6 carbon atoms. Preferably $R_7$ and $R_8$ are H and; thus, $R_2$ is $NH_2$.

The $R_3$ Substituents

The $R_3$ substituent is at the 3-position on the steroid nucleus. There are three (3) possible $R_3$ substituents. $R_3$ can be an oligosaccharide-containing residue having the following structure:

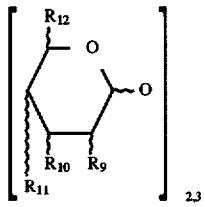

where $R_9$ is hydrogen; methyl; hydroxy; carboxy; acetoxy; arylalkyloxy or benzoxy; $R_{10}$ is hydrogen; methyl; carboxy; acetoxy; arylalkyloxy; heteroarylalkyloxy; benzoxy or hydroxy; $R_{11}$ is oxygen, wherein further when $R_{11}$ is a substituent on the terminal monosaccharide sugar residue, $R_{11}$ is OH, methyl; acetoxy; arylalkyloxy; heteroarylalkyloxy; and $R_{12}$ is a hydrogen, methyl, methylhydroxymethyl, or acetoxymethyl. In the compounds of the present invention, when $R_{11}$ is oxygen, said oxygen serves to link the monosaccharide residues via a glycoside linkage.

The oligosaccharide residue can be comprised of two or three monosaccharide units, preferably three monosaccharide units. Said monosaccharide units may be the same or different. Preferred monosaccharide units are dideoxyribohexopyranose and rhamnopyranose.

Preferred $R_9$ substituents are hydrogen, methyl and hydroxy. Most preferred $R_9$ is hydrogen. Preferred $R_{10}$ substituents are hydrogen, methyl and hydroxy. Most preferred $R_{10}$ is hydroxy. $R_{11}$ is oxygen, except when $R_{11}$ is a substituent on the terminal monosaccharide sugar residue of the oligosaccharide sugar residue. The preferred $R_{11}$ substituent on the terminal monosaccharide sugar residue is hydroxy.

Preferred $R_{12}$ substituents are hydrogen and methyl. The most preferred $R_{12}$ substituent is methyl.

$R_3$ is also an oligosaccharide-containing residue having the following structure:

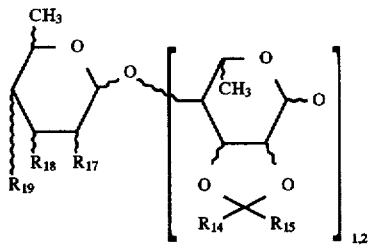

where $R_{14}$ and $R_{15}$, which may be the same or different, are hydrogen; 1–6 carbon lower alkyl; arylalkyl; heteroarylalkyl; heteroaryl or aryl; $R_{17}$ can be hydrogen, hydroxy, acetoxy or benzoxy; $R_{18}$ and $R_{19}$ are hydroxy, acetoxy and benzoxy;

The oligosaccharide residue can be comprised of two or three monosaccharide units, preferably three monosaccharide units. Said monosaccharide units may be the same or different. Preferred monosaccharide units are dideoxyribohexopyranose and rhamnopyranose.

Preferred $R_{14}$ substituents are hydrogen and a 1–6 carbon lower alkyl. The more preferred $R_{14}$ substituent is a 1–6 carbon lower alkyl. The most preferred $R_{14}$ substituent is a methyl group. Preferred $R_{15}$ substituents are hydrogen and a 1–6 carbon lower alkyl. The more preferred $R_{15}$ substituent is a 1–6 carbon lower alkyl. The most preferred $R_{15}$ substituent is a methyl group. Preferred $R_{17}$ substituents are hydrogen, acetoxy and hydroxy. The most preferred $R_{17}$ substituent is hydrogen. Preferred $R_{18}$ are substituents are hydroxy and acetoxy. The most preferred $R_{18}$ substituent is hydroxy. Preferred $R_{19}$ substituents are hydroxy and acetoxy. The most preferred $R_{19}$ substituent is hydroxy.

Finally, $R_3$ is an oligosaccharide residue having the following structure:

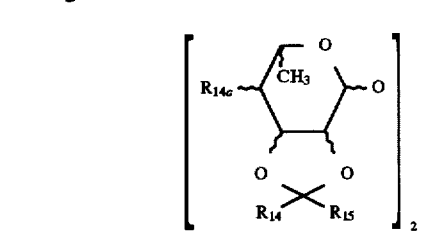

wherein $R_{14}$ and $R_{15}$ which may be the same or different, are hydrogen, 1–6 carbon lower alkyl, arylalkyl; heteroarylalkyl; heteroaryl or aryl; $R_{14a}$ is oxygen; wherein further when $R_{14a}$ is a substituent on the terminal monosaccharide residue, $R_{14a}$ must be hydroxy, methyl, acetoxy, arylalkyloxy or heteroarylalkyloxy. In the compounds of the present invention, when $R_{14a}$ is oxygen, said oxygen serves to link the monosaccharide residues via a glycoside linkage.

The oligosaccharide residue can be comprised of two or three monosaccharide units, preferably three monosaccharide units. Said monosaccharide units may be the same or different. Preferred monosaccharide units are dideoxyribohexopyranose and rhamnopyranose.

Preferred $R_{14}$ and $R_{15}$ are 1–6 carbon lower alkyl and the most preferred $R_{14}$ and $R_{15}$ is methyl. When $R_{14a}$ is a substituent on the terminal monosaccharide residue, the preferred $R_{14a}$ is hydroxy.

The $R_4$ Substituents

The $R_4$ substituent is at the 12-position on the steroid nucleus. $R_4$ can be OH, H or $OR_{13}$, where $R_{13}$ is a monosaccharide sugar residue; acetoxy; benzoxy; arylalkyl; or heteroarylalkyl. The preferred $R_4$ substituents are H or $OR_{13}$, where $R_{13}$ is a monosaccharide residue. Said monosaccharide residue is selected from hexose, 2-deoxyglucose, 6-deoxyhexose, 2,6-dideoxyhexose, rhamnose, a glucose and arabinose, a digitoxose, a fructose, a galactose, rhamnopyranose, hexopyranose, 6-deoxyglucose, 4,6-dideoxy-glycopyrainose, mannose, cymarose, xylose, lyxose, ribose, digitalose, glucosamine, 4-amino-2,4,6-trideoxylyxohexopyranose, 4-amino-4,6-dideoxy glycopyranose, 2,3-dideoxyrhamnopyranose, 4-methoxy-4,6-dideoxyrhamnopyranose, preferably the β-D or α-L anomers thereof.

The most preferred $R_4$ substituent is H.

Z

Z is —CH—, where a and b are single bonds, or =C, where either a or b is a double bond. The preferred Z is —CH where a and b are single bonds.

Preferred oligosaccharide-containing 14-aminosteroid compounds of the present invention are:

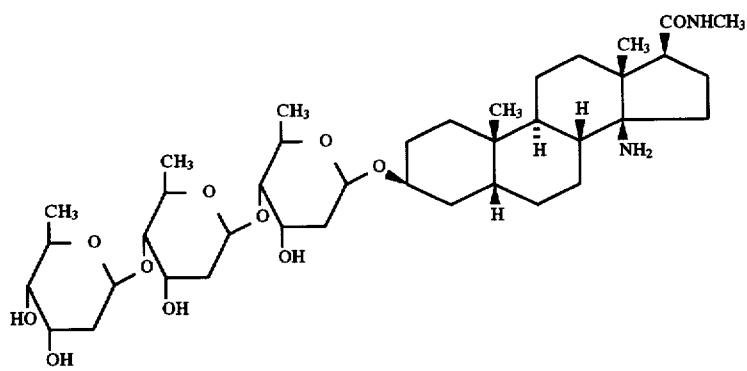

(3β,5β,14β,17β)-14-Amino-3-[(O-2,6-dideoxy-
β-D-ribo-hexopyranosyl-(1→4)-O-2,6-dideoxy-
β-D-ribo-hexopyranosyl(1→4)-2,6-dideoxy-
β-D-ribo-hexopyranosyl)oxy]-N-methylandrostane-
17-carboxamide

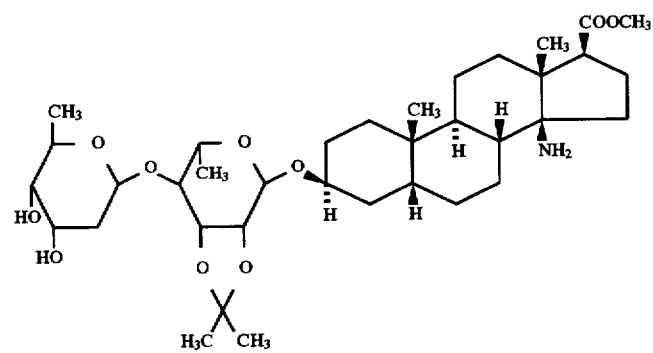

(3β,5β,14β,17β)-14-Amino-3-[[O-2,6-dideoxy-
b-D-ribo-hexopyranosyl-(1→4)-6-deoxy-2,3-O-(1-
methylethylidene)-α-L-mannopyranosyl]oxy]androstane-
17-carboxylic acid, methyl ester

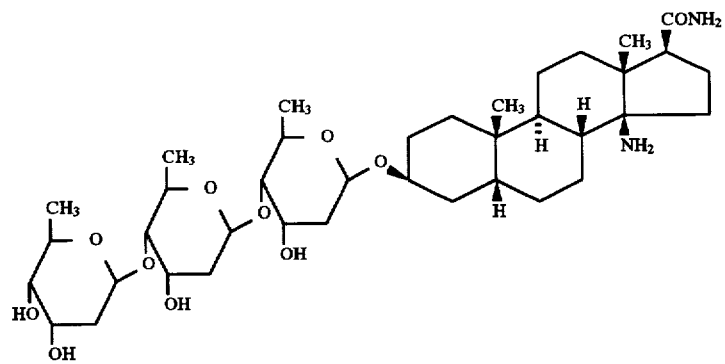

(3β,5β,14β,17β)-14-Amino-3-[(O-2,6-dideoxy-
β-D-ribo-hexopyranosyl-(1→4)-O-2,6-dideoxy-
β-D-ribo-hexopyranosyl-(1→4)-2,6-dideoxy-
β-D-ribo-hexopyranosyl)oxy]androstane-17-carboxamide -continued

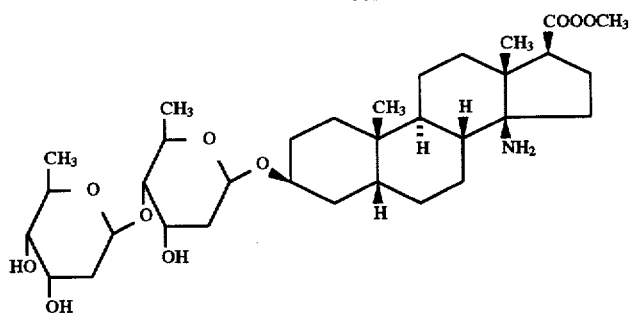

(3β,5β,14β,17β)-14-Amino-3-[(O-2,6-dideoxy-
β-D-ribo-hexopyranosyl-(1→4)-2,6-dideoxy-
β-D-ribo-hexopyranosyl)oxy]androstane-17-carboxylic
acid, methyl ester

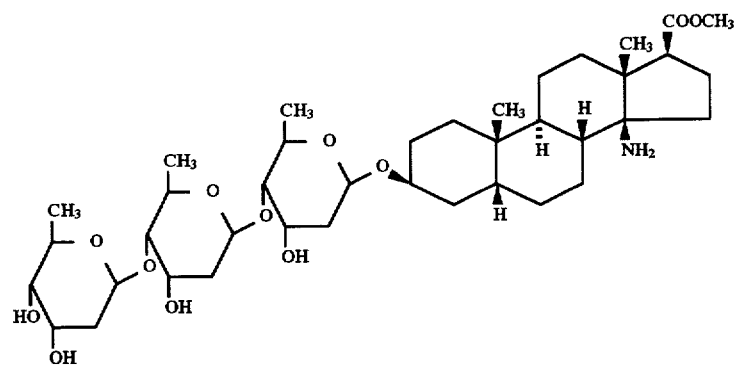

(3β,5β,14β,17β)-14-Amino-3-[(O-2,6-dideoxy-β-D-
ribo-hexopyranosyl-(1→4)-O-2,6-dideoxy-β-D-ribo-
hexopyranosyl-(1→4)-2,6-dideoxy-β-D-ribo-hexo-
pyranosyl)oxy]androstane-17-carboxylic acid, methyl ester

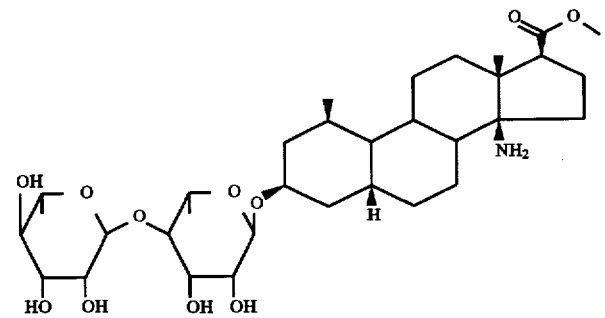

14β-amino-3β-[α-(L)-rhamnopyranosyloxy-
(1→4)-α-(L)-rhamnopyranosyloxy]-5β-androstane-17β-carboxylic
acid, methyl ester

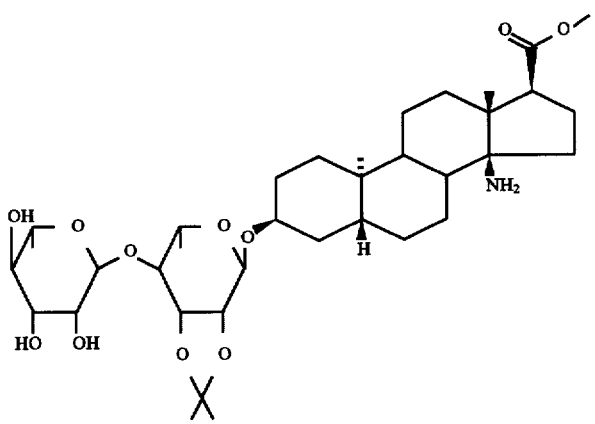

14β-amino-3β-[α-(L)-rhamnopyranosyloxy-(1→4)-2',3',-O-
isopropylidene-α-(L)-rhamnopyranosyloxy]-5β-androstane-17β-
carboxylic acid, methyl ester

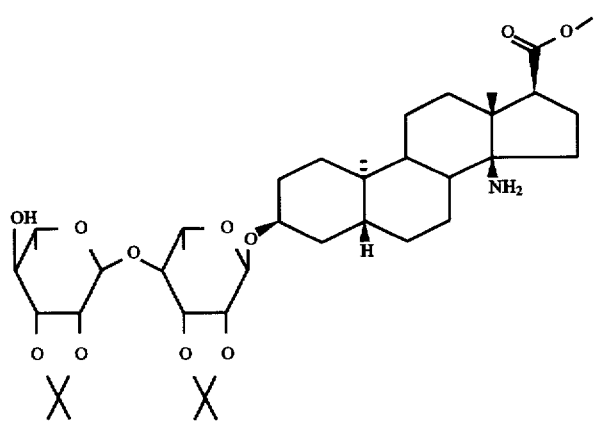

14β-amino-3β-[2",3"-O-isopropylidene-α-(L)-rhamnopyranosyl-
oxy-(1→4)-2',3'-O-isopropylidene-α-(L)-rhamnopyranosyloxy]-
5β-androstane-17β-carboxylic acid, methyl ester

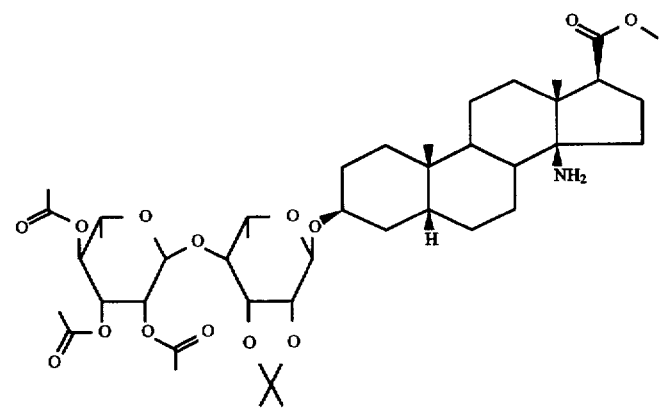

14β-amino-3β-[2",3",4"-tri-O-acetyl-α-(L)-rhamnopyranosyloxy-
(1→4)-2',3'-O-isopropylidene-α-(L)-rhamnopyranosyloxy]-5β-
androstane-17β-carboxylic acid, methyl ester

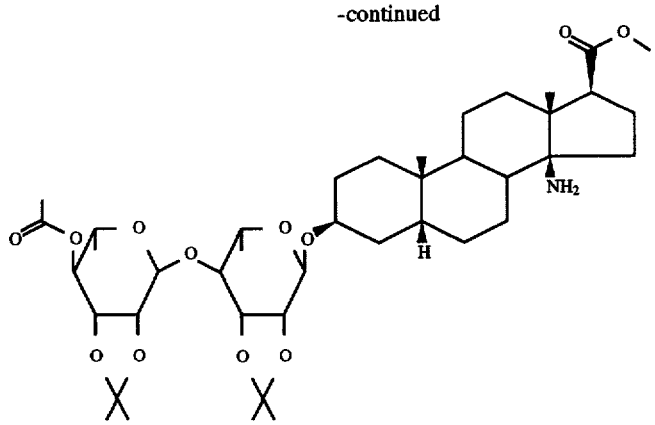

14β-[4"-O-acetyl-2",3"-O-isopropylidene-β-(L)-
rhamnopyranosyloxy-(1→4)-2',3'-O-isopropylidene-α-(L)-
rhamnopyranosyloxy]-5β-androstane-17β-carboxylic acid, methyl ester

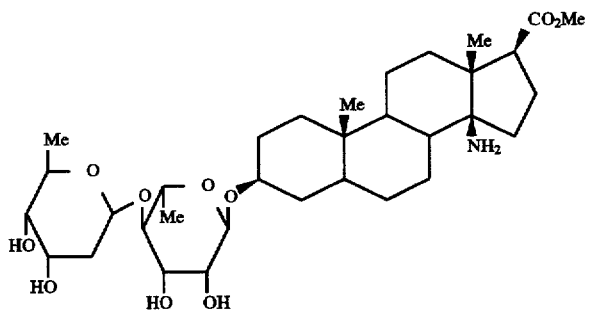

(3β,5β,16β,17β)-14-Amino-3-[(2,6-dideoxy-β-D-ribo-hexopyranosyl-
(1→4)-6-deoxy-α-L-mannopyranosyl)-oxy]-androstane-17-carboxylic
acid methyl ester

PREPARATION OF THE OLIGOSACCHARIDE-CONTAINING 14-AMINOSTEROID COMPOUNDS OF THE PRESENT INVENTION

The present invention also encompasses a process for introducing an amino group at the 14-position on the steroid nucleus. Prior art chemistry, according to U.S. Pat. Nos. 4,325,879; 4,552,868; 4,552,868; 4,584,289; and 4,885,280, incorporated by reference herein, utilized hydrazoic acid to introduce an azide moiety at the 14-position on the steroid nucleus. The azide moiety was then reduced to the 14-position amino group on the steroid nucleus. The present process which involves use of iodoisocyanate is an improvement in the art because it eliminates hazardous hydrazoic acid; is more readily adaptable to larger scale manufacturing operations; provides better yields of the 14-aminosteroid compound and; allows introduction of the 14-position amino group in the presence of other acid-sensitive functionalities on the steroid nucleus. The oligosaccharide residue on the 3-position of the steroid nucleus is an acid sensitive moiety, particularly susceptible to hydrazoic acid cleavage. Thus, the use of the iodoisocyanate chemistry eliminates the problem of cleaving the oligosaccharide residue from the steroid nucleus.

The process of the present invention diastereoselectively introduces an amino group on the 14-position of the steroid nucleus by adding iodoisocyanate to the 14–15 position double bond on the steroid nucleus, followed by dehalogenation, and conversion of the isocyanate to the amine moiety. After the addition of the iodoisocyanate to the 14–15 position double bond, the iodo group is removed via a dehalogenation reaction and then the isocyanate is converted to the 14-position amino group.

Specifically, the process of the present invention comprises:

a.) In situ generation of iodoisocyanate using preferably, but not limited to, silver cyanate and iodine in a suitable solvent including but not limited to, esters such as ethyl acetate, isopropyl acetate, or propyl acetate, nitriles such as acetonitrile or propionitrile, halogenated hydrocarbons such as methylene chloride, chloroform or dichloroethane, ethers such as tetrahydrofuran or tertiary-butyl methyl ether, or mixtures thereof. Preferred solvents include a mixture of nitriles, more preferably acetonitrile, with esters or ethers, most preferably ethyl acetate or tertiary-butyl methyl ether. The temperature for the iodoisocyanate addition may range from –30° C. to 100° C., most preferably –10° C. to 5° C. The reaction time for the isocyanate addition may range from 1 to 6 hours, preferably 1 to 3 hours. The reagents may be added together in any order and at any rate, most preferably iodine is added in solvent to a mixture of the steroid and silver cyanate in solvent over a period of 30 to 60 minutes;

b.) dehalogenation preferably by treatment with an organotin hydride reagent including but not limited to alkyltin hydrides such as tri-n-butyltin hydride or aryltin hydrides such as diphenyltin hydride or triphenyltin hydride and a radical initiator including but not limited to 2,2'-azobisisobutyronitrile (AIBN) or peroxides such as benzoylperoxide or tertiary-laurylperoxide in a suitable solvent including but not limited to esters such as ethyl acetate, isopropyl acetate or propyl acetate, nitriles such as acetonitrile or propionitrile, halogenated hydrocarbons such as methylene chloride, chloroform or dichloroethane, ethers such as diethyl ether, tetrahydrofuran or tertiary-butyl methyl ether, hydrocarbons such as hexanes or heptanes, aromatics such as benzene or toluene or mixtures thereof. Preferred solvents include aromatics, more preferably toluene and halogenated hydrocarbons, most preferably methylene chloride. The reaction temperature for the dehalogenation may range from 0° C. to 100° C., most preferably 15° C. to 30° C. The reaction time may range from 1 to 6 hours, most preferably 2 to 4 hours; and c.) aqueous hydrolysis of the isocyanate group to the amine using strong acids including but not limited to hydrochloric acid, sulfuric acid, hydrobromic acid or trifluoroacetic acid, or bases including but not limited to lithium hydroxide, sodium hydroxide, potassium hydroxide, lithium carbonate, sodium carbonate, potassium carbonate or other bases capable of generating hydroxide ions in aqueous media such as triethylamine or pyridine. Suitable co-solvents for the hydrolysis reaction include but are not limited to water miscible nitriles such as acetonitrile or propionitrile, water miscible ethers such as tetrahydrofuran, dimethoxyethane or dioxane, or other water miscible solvents such as N,N'-dimethylformamide or dimethyl sulfoxide or mixtures thereof. Preferred solvents include water miscible nitriles, more preferably acetonitrile, and water miscible ethers, most preferably tetrahydrofuran, dimethoxyethane and dioxane. The reaction temperature for the hydrolysis reaction may range from 0° C. to 60° C., for the acid catalyzed hydrolysis, most preferably 15° C. to 30° C., and may range from ambient temperature to 100° C. for the based catalyzed hydrolysis, most preferably 80° C. to 100° C. The reaction time for the acid catalyzed hydrolysis may range from 4 to 72 hours, most preferably 12 to 36 hours, and may range from 2 to 48 hours for the base catalyzed hydrolysis, most preferably 2 to 12 hours. The following non-limiting examples are illustrative of the iodoisocyanate process for introducing an amino group at the 14-position on the steroid nucleus.

EXAMPLE 1

(3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17-carboxylic acid, methyl ester

A.

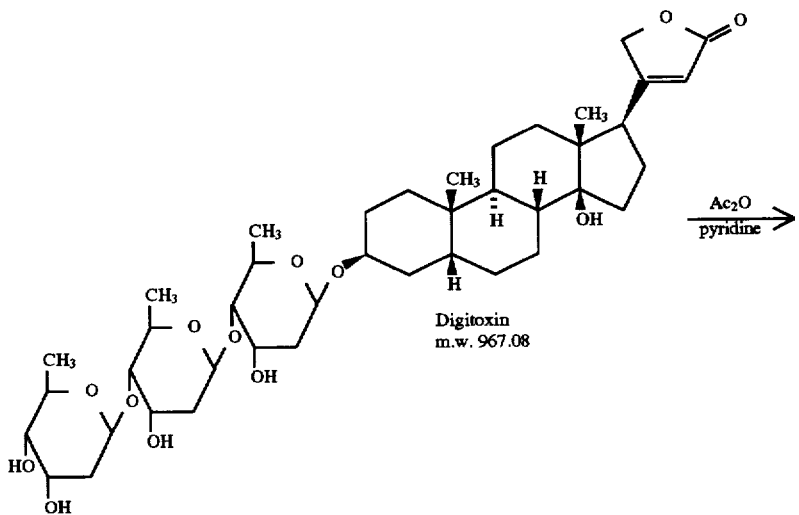

-continued
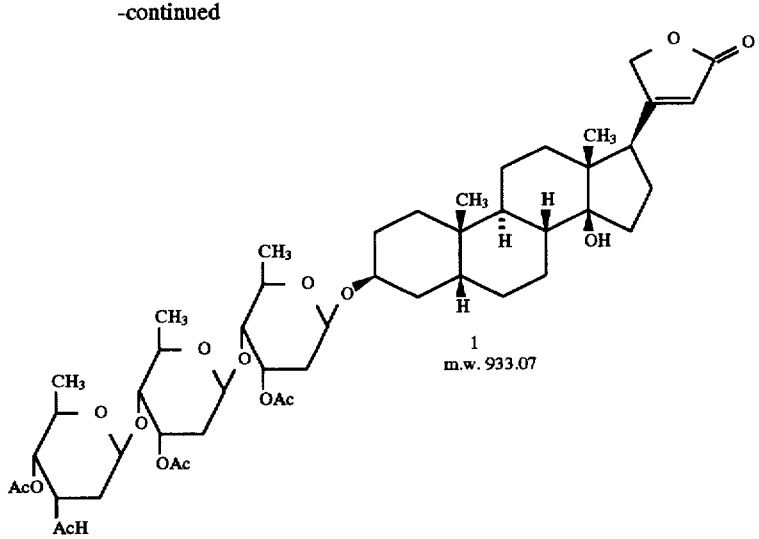
1
m.w. 933.07
B.
1 →[O₃, K₂CO₃]
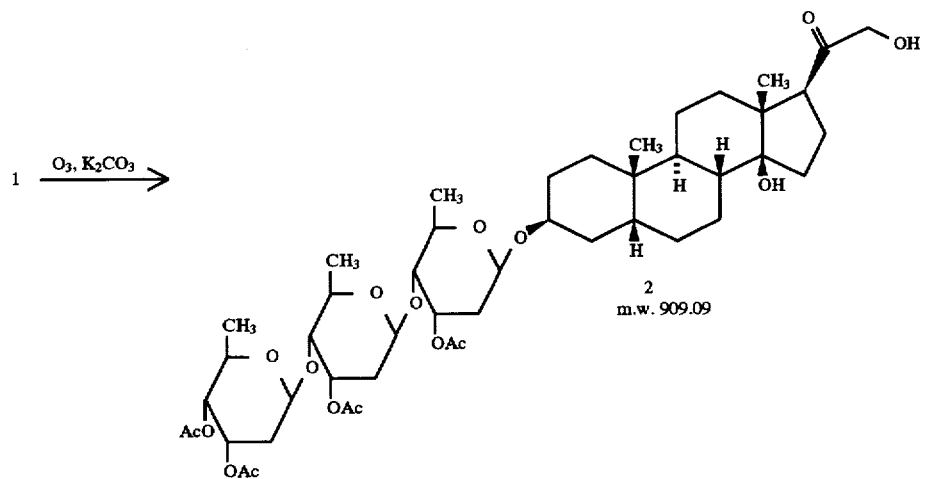
2
m.w. 909.09
C.
2 →[K₂CO₃, NaIO₄]
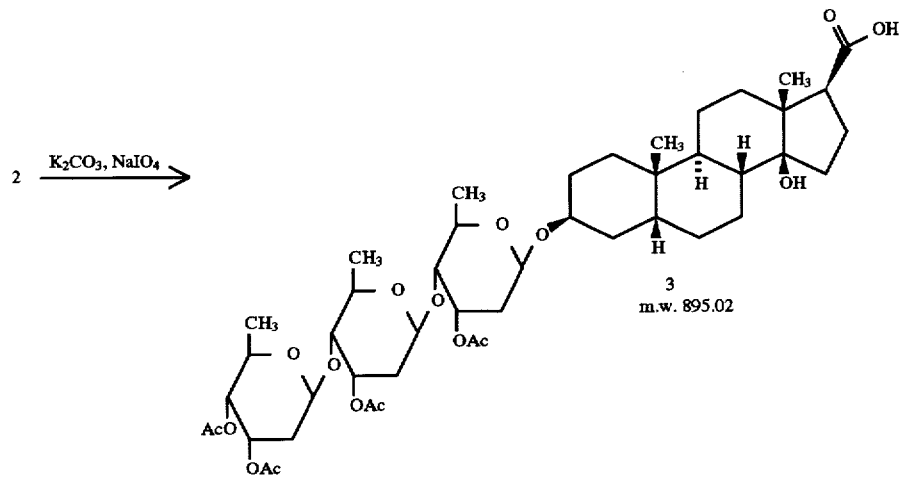
3
m.w. 895.02

D.
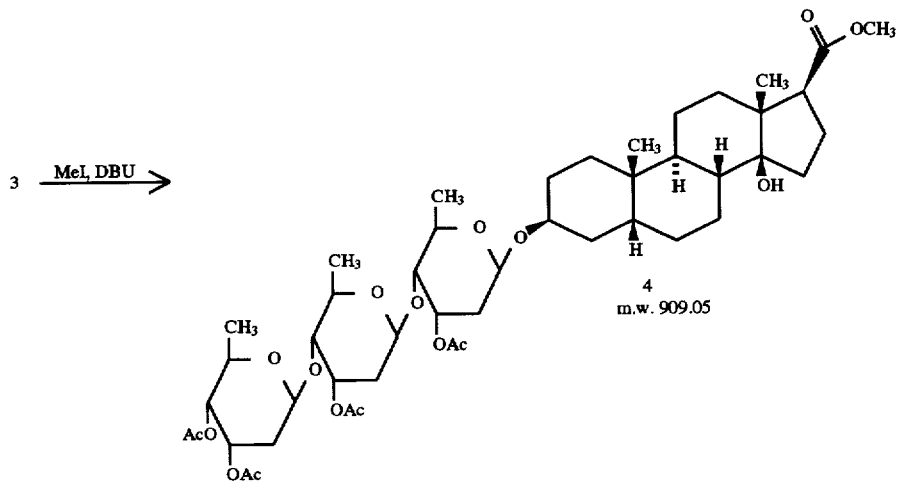
E.
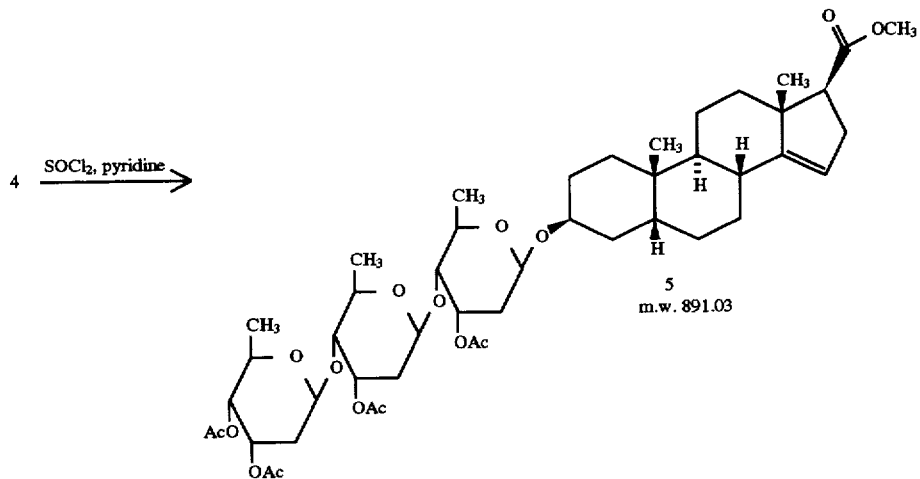
F.
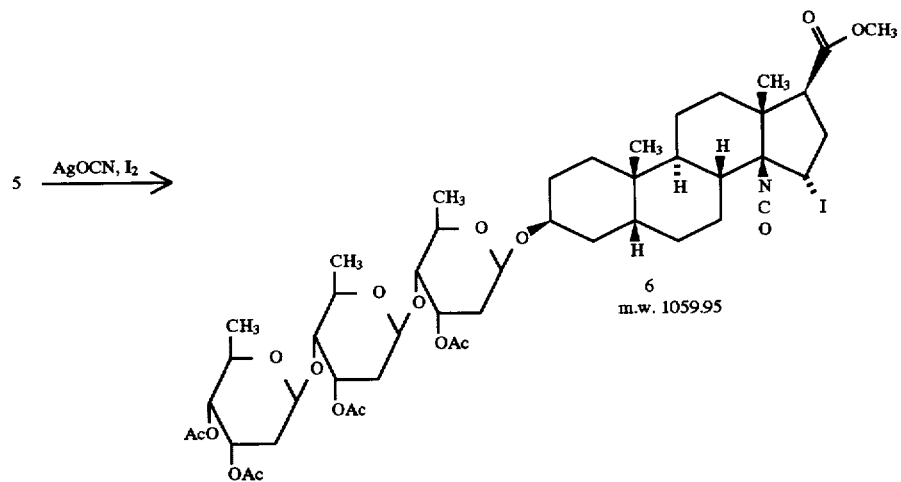

G.

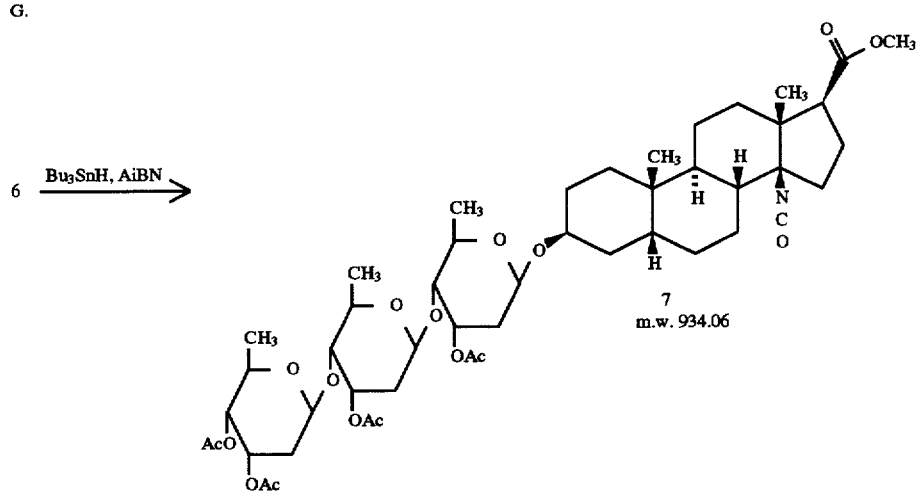

H.

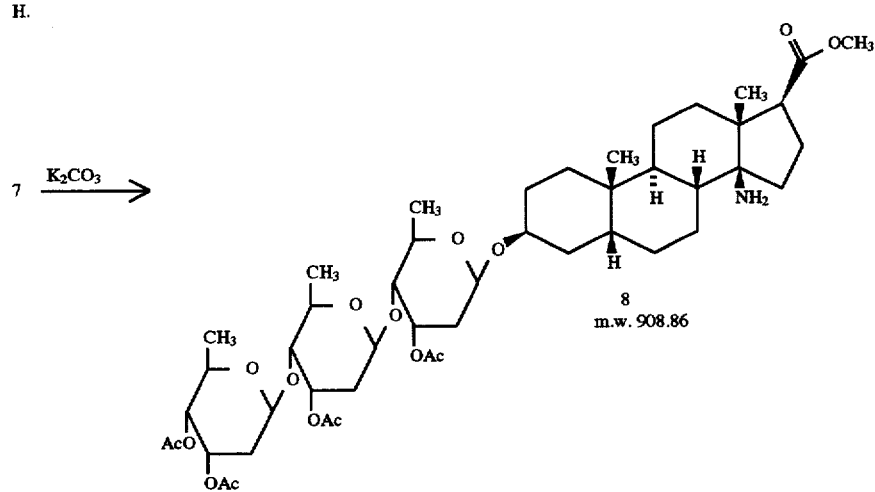

I.

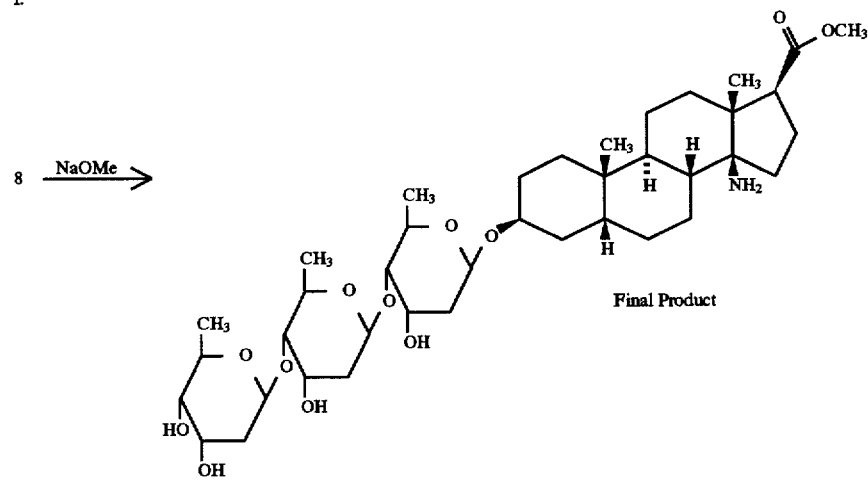

A. (3β,5β)-3[(O-3,4-Di-O-acetyl-2,6-dideoxy-β-D-ribo-hexopyranosyl-(1→4)-O-3O-acetyl-2,6-dideoxy-β-D-ribo-hexopyranosyl-(1→4)-3-O-acetyl-2,6-dideoxy-β-D-ribo-hexopyranosyl)oxy]-14-hydroxycard-20 (22)-enolide Digitoxin (2.0 g, 0.0026 mol) is dissolved in anhydrous pyridine (50 ml). Anhydrous acetic anhydride (25 ml) is added and the solution is heated to 80° C. for 3 hrs. Upon cooling to ambient temperature, the reaction is poured into ice/water (500 ml) forming an amber solid. The mixture is extracted with methylene chloride (2×100 ml). The organic layers are combined, washed with saturated aqueous sodium bicarbonate solution (2×100 ml), saturated aqueous sodium chloride solution (1×100 ml), dried (magnesium sulfate), treated with darco and filtered. The filtrate is concentrated under reduced pressure to a solid. The traces of pyridine are removed by azeotropic distillation with toluene (2×20 ml) and then methanol (2×20 ml) to yield 1.8 g (74%) of 1 as a white solid.

B. (3β,5β,14β,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl-(1→4)-3-O-acetyl-2,6-dideoxy-β-D-ribo-hexopyranosyl)oxy]-14,21-dihydroxy-pregan-20-one Compound 1 (0.3 g, 0.001 mol) is dissolved in methylene chloride (100 ml) and cooled to −78° C. The cooled solution is treated with ozone for 8 min resulting in a persistent blue color. At this point, ozone addition is discontinued and the reaction is allowed to stir for an additional 0.5 hr. Oxygen is then bubbled through the solution at a moderate rate for 15 min. followed by nitrogen until the blue color disappears. The reaction is allowed to reach ambient temperature and saturated aqueous potassium carbonate solution (50 ml) is added and the resulting mixture is allowed to stir for 20 hrs. The two phases are separated and the organic phase is washed with water (1×50 ml), saturated aqueous sodium chloride solution (1×50 ml), dried (magnesium sulfate) and filtered. The filtrate is concentrated under reduced pressure to a white foamy solid. The solid is chromatographed on silica gel (230–400 mesh) using 97:3 methylene chloride:methanol as the eluent. Fractions containing the pure product are combined, concentrated under reduced pressure and dried in vacuo for 24 hrs to yield 0.6 g (62%) of 2 as a white solid. The NMR and mass spectrum are consistent with the structure. This compound is carried on to the next step.

C. (3β,5β,14β,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl-(1→4)-3-O-acetyl-2,6-dideoxy-β-D-ribo-hexopyranosyl)oxy]-14-hydroxyandrostane-17-carboxylic Acid To a solution of compound 2 (17 g, 0.187 mol) in acetone (200 ml) is added a solution of potassium carbonate (3.88 g, 0.028 mol) in water (25 ml), followed by a solution of sodium periodate (12 g, 0.056 mol) in water (50 ml). The resulting mixture is stirred at ambient temperature for 24 hrs. The reaction is diluted with water (250 ml) then acidified to a pH of 1 with 1N hydrochloric acid. Once acidic, the solution is quickly extracted with methylene chloride (2×300 ml). The combined organic layers are washed with 5% aqueous hydrochloride acid (1×200 ml), water (1×200 ml), dried (magnesium sulfate) and filtered. The filtrate is concentrated under reduced pressure to a white solid. The solid is chromatographed on silica gel using 97.5:2.5 methylene chloride:methanol as the eluent. Fractions containing the pure product are combined and concentrated under reduced pressure to yield 16.2 g (97%) of) as a white solid. This compound is carried on to the next step.

D. (3β,5β,14β,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl-(1→4)-3-O-acetyl-2,6-dideoxy-β-D-ribo-hexopyranosyl)oxy]-14-hydroxyandrostane-17-carboxylic Acid, Methyl Ester To a solution of compound 3 (15 g, 0.017 mol) in anhydrous acetonitrile (100 ml) is added 1,8-diazabicyclo[5.4.0]undec-7-ene (DBU, 2.4 ml, 2.89 g, 0.019 mol) followed by iodomethane (1.18 ml, 2.7 g, 0.019 mol). The resulting solution is allowed to stir at ambient temperature for 20 hrs. The reaction is diluted with water (1 l) and extracted with methylene chloride (5×200 ml). The combined extracts are washed with saturated aqueous sodium chloride solution (2×200 ml), dried (magnesium sulfate) and filtered. The filtrate is concentrated under reduced pressure to a solid. The solid is chromatographed on silica gel (230–400 mesh) using 99:1 methylene chloride:methanol as the eluent. Fractions containing the pure product are concentrated under reduced pressure to a solid which is dried in vacuo to yield 13.68 g (90%) of 4 as a white solid. This compound is carried on to the next step.

E. (3β,5β,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl-(1→4)-3-O-acetyl-2,6-dideoxy-β-D-ribo-hexopyranosyl)oxy]androst-14-ene-17-carboxylic Acid Methyl Ester Compound 4 (4.02 g, 0.0044 mol) is dissolved in anhydrous pyridine (20 ml) and the solution is cooled to −5° C. in an ice/methanol bath. A solution of thionyl chloride (5 ml) in anhydrous pyridine (5 ml) is added dropwise over 25 min. The reaction is then poured into ice water (400 ml) and stirred until the ice melted (10 min). The resulting mixture is extracted with ethyl acetate (3×150 ml). The combined extracts are washed with 1N hydrochloric acid (1×100 ml), water (2×100 ml), saturated aqueous sodium bicarbonate solution (2×100 ml), saturated aqueous sodium chloride solution (1×100 ml), dried (magnesium sulfate) and filtered. The filtrate is concentrated under reduced pressure to a foamy solid. The solid is chromatographed on silica gel (230–400 mesh) using 30:70 ethyl acetate:hexanes as the eluent. Fractions containing the pure product are combined and concentrated under reduced pressure to yield 3.26 g (83%) of 5 as a white solid. This compound is carried on to the next step.

F. (3β,5β,14β, 15α,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl-(1→4)-3-O-acetyl-2,6-dideoxy-β-D-ribo-hexopyranosyl)oxy]-15-iodo-14-isocyanato-androstane-17-carboxylic Acid, Methyl Ester Compound 5 (0.27 g, 0.3 mmol) is dissolved in ethyl acetate (1.35 ml) and acetonitrile (2.7 ml) and the solution is cooled to 1° C. in an ice/methanol bath. Silver cyanate (0.054 g, 0.36 mmol) is added followed by the dropwise addition of iodine (0.081 g, 0.32 mmol) in ethyl acetate (4 ml). Upon completion of the iodine addition (20 min) the reaction is allowed to continue stirring cold for an additional 1.5 hr. The reaction is then diluted with ethyl acetate (20 ml) and filtered through celite. The filtrate is washed with 1% aqueous sodium sulfite solution (1×10 ml) and the organic layer is then concentrated under reduced pressure to yield 0.32 g (99%) of 6 as a foamy solid. This compound is carried on to the next step.

G. (3β,5β,14β,17β)-3-[(O-3,4-Di-O-acetyl-2,6-dideoxy-β-D-ribo-hexopyranosyl-(1→4)-O-3O-acetyl-2,6-dideoxy-β-D-ribo-hexopyranosyl-(1→4)-3-O-acetyl-2,6-dideoxy-β-D-ribo-hexopyranosyl)oxy]-14-isocyanato-androstane-17-carboxylic Acid Methyl Ester In a flame-dried apparatus under a nitrogen atmosphere is dissolved 6 (0.32 g, 0.3 mmol) in anhydrous methylene chloride (10 ml). To this solution is added catalytic 2,2'-azobisisobutyronitrile (AIBN, 0.003 g) followed by tributyltin hydride (0.085 ml, 0.091 g, 0.31 mmol). The resulting solution is allowed to stir at ambient temperature for 1 hr then was concentrated under reduced pressure to an oil. The oil was triturated with hexanes to form a white solid which was collected by filtration and air dried to yield 0.25 g (89%) of 7. This compound is carried on to the next step.

H. (3β,5β,14β,17β)-3-[(O-3, 4-Di-O-acetyl-2,6-dideoxy-β-D-ribo-hexopyranosyl-(1→4)-O-3O-acetyl-2,6-dideoxy-β-D-ribo-hexopyranosyl-(1→4)-3-O-acetyl-2,6-dideoxy-β-D-ribo-hexopyranosyl)oxy]-14 amino-androstane-17-carboxylic Acid, Methyl Ester To a solution of compound 7 (0.3 g, 0.32 mmol) in acetonitrile (15 ml) is added a solution of potassium carbonate (0.66 g, 4.8 mmol, 15 eq) in water (10 ml). The reaction is stirred at reflux temperature for 4 hrs. Upon cooling to room temperature, the reaction is concentrated under reduced pressure to remove the acetonitrile. To the remaining aqueous residue is added water (20 ml) and the mixture is acidified with 1N hydrochloric acid to a pH of 1, then quickly made basic (pH 9) with concentrated ammonium hydroxide. The aqueous mixture is extracted with methylene chloride (2×30 ml) and the combined layers are dried (magnesium sulfate) and filtered. The filtrate is concentrated under reduced pressure to a solid which is dried in vacuo yielding 0.23 g (7%) of crude 8. This compound is used directly in the next step.

I. (3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17-carboxylic Acid, Methyl Ester In a flame-dried apparatus under a nitrogen atmosphere is dissolved compound 8 (0.23 g, 0.3 mmol) in anhydrous methanol (9 ml). A solution of sodium methoxide (0.063 g, 1.2 mmol, 4 eq) in anhydrous methanol (2 ml) is added and the reaction is allowed to stir at ambient temperature for 3 hrs. The reaction is then concentrated under reduced pressure to a white residue. The residue is dissolved in water (30 ml) and cooled in an ice/water bath. The solution is acidified with 1N hydrochloric acid to a pH of 1 then quickly made basic (pH 9) with concentrated ammonium hydroxide. The aqueous mixture is extracted with methylene chloride (2×30 ml). The combined extracts are dried (magnesium sulfate) and filtered. The filtrate is concentrated under reduced pressure to a solid. The solid is chromatographed on silica gel (230–400 mesh) using 9:1 methylene chloride:methanol containing 0.5% concentrated ammonium hydroxide as the eluent. Fractions containing the pure product are combined and concentrated under reduced pressure to a solid which is dried in vacuo yielding the (3β,5β,14β,17β,)-14-amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17-carboxylic acid, methyl ester, Final Product.

EXAMPLE 2

(3β,5β,14β,17β,)-14-Amino-3-[(O-2,6-dideoxy-β-D-ribo-hexopyranosyl-(1→4)-O-2,6-dideoxy-β-D-ribo-hexopyranosyl)oxyl-androstane-17-carboxylic acid, methyl ester

A.

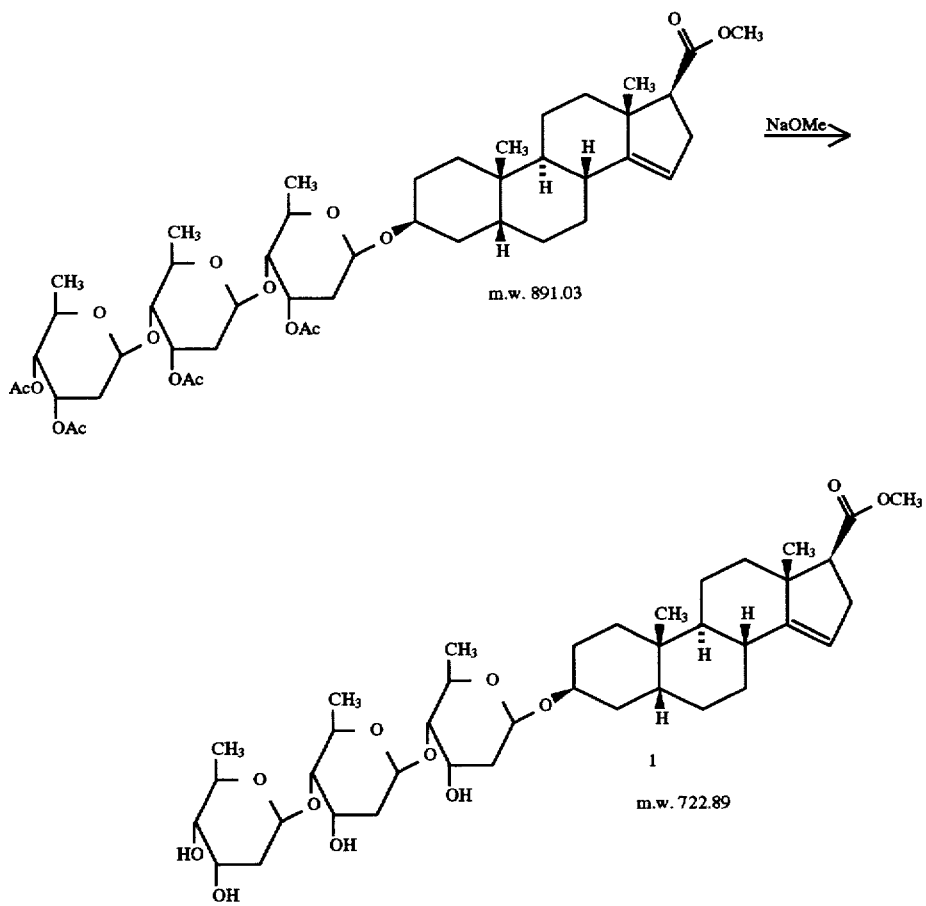

B.
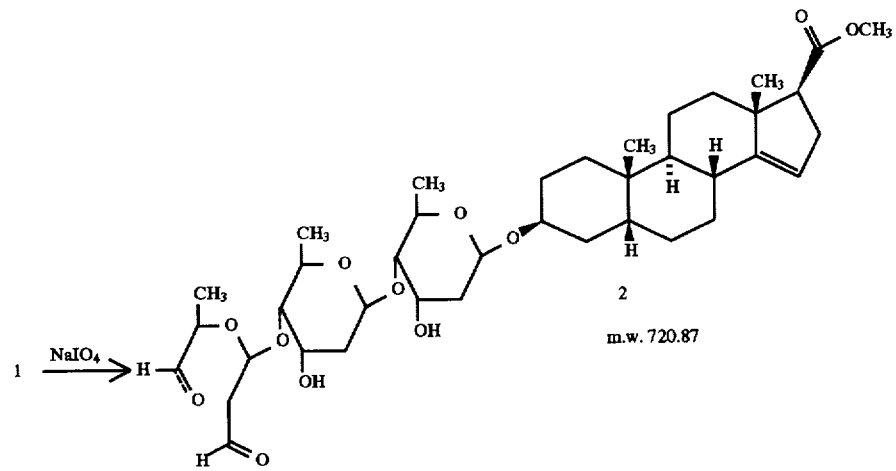
C.
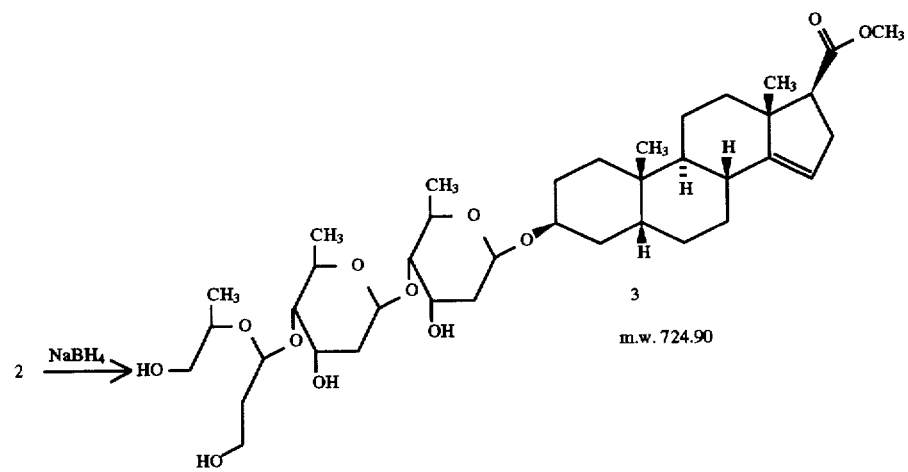
D.
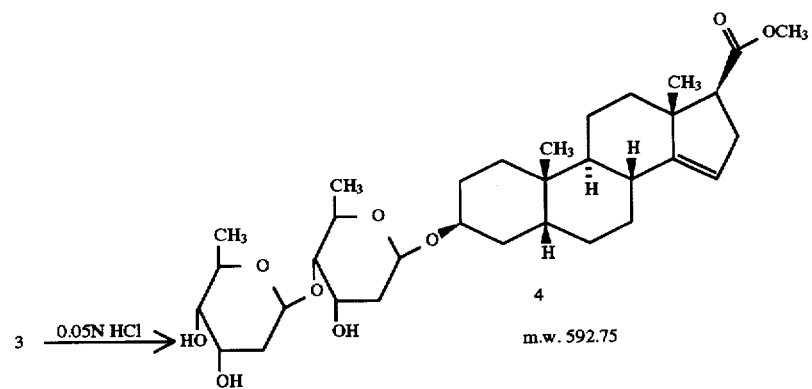

E.
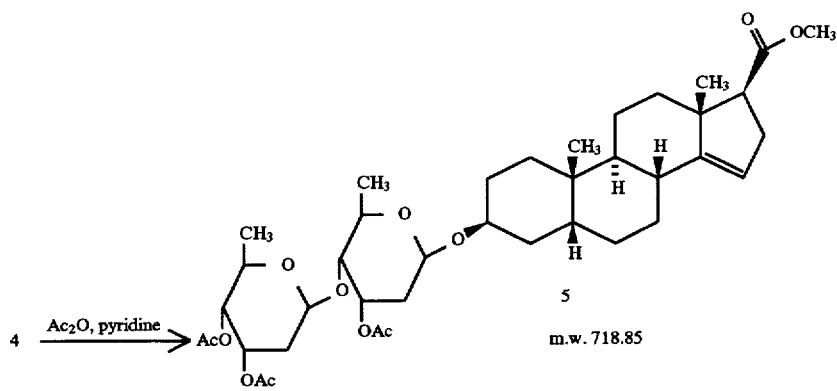
F.
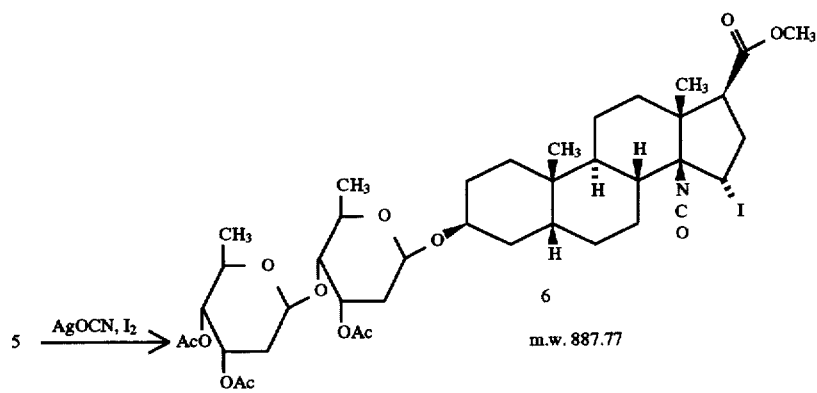
G.
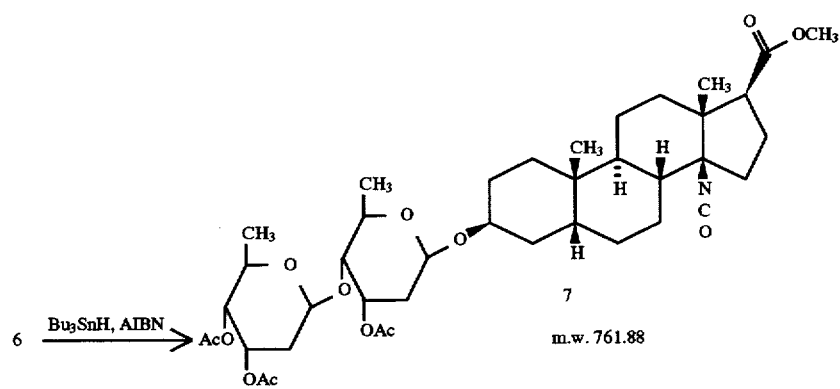
H.
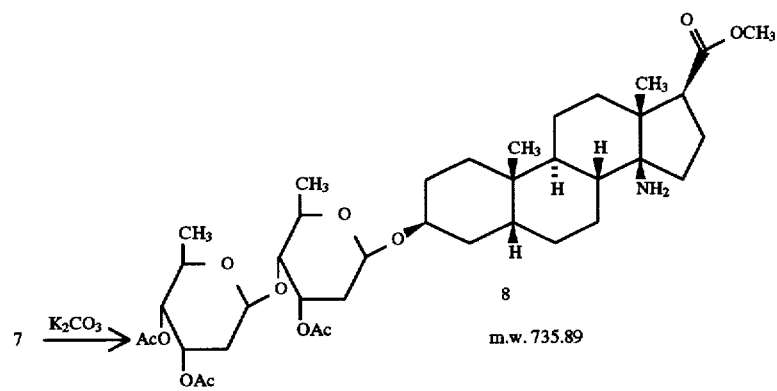

L.

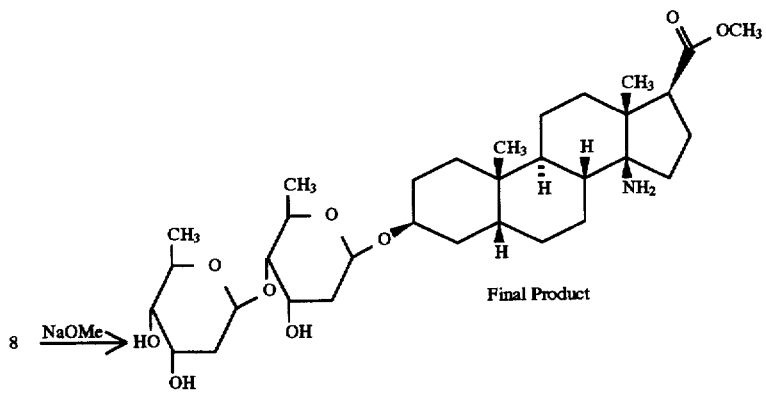

Final Product

A. (3β,5β,17β)-3-[(O-2,6-dideoxy-β-D-ribo-hexopyranosyl-(1→4)-O-2, 6-dideoxy-β-D-ribo-hexopyranosyl-(1→4)-2,6-dideoxy-β-D-ribo-hexopyranosyl)oxy]androst-14-ene-17-carboxylic Acid Methyl Ester For the preparation of (3β,5β,17β)-3-[(O-3, 4-Di-O-acetyl-2,6-dideoxy-β-D-ribo-hexopyranosyl-(1→4)-O-3-O-acetyl-2,6-dideoxy-β-D-ribo-hexopyranosyl-(1→4)-3-O-acetyl-2,6-dideoxy-β-D-ribo-hexopyranosyl)oxy]androst-14-ene-17-carboxylic acid methyl ester, refer to the preparation of Example 2 hereinbefore.

In a flame dried apparatus under a nitrogen atmosphere, (3β,5β, 17β)-3-[(O-3,4-Di-O-acetyl-2,6-dideoxy-β-D-ribo-hexopyranosyl-(1→4)-O-3O-acetyl-2,6-dideoxy-β-D-ribo-hexopyranosyl-(1→4)-3-O-acetyl-2,6-dideoxy-β-D-ribo-hexopyranosyl)oxy]androst-14-ene-17-carboxylic acid methyl ester (2.29 g, 0.0025 mol) is dissolved in anhydrous methanol (50 ml). A solution of sodium methoxide (0.72 g, 0.014 mol) in anhydrous methanol (10 ml) is added and the reaction is allowed to stir at ambient temperature for 3 hrs. The reaction is concentrated under reduced pressure to a solid which is then dissolved in water (50 ml). The mixture is acidified to a pH of 1 with 1N hydrochloric acid, then quickly made basic (pH 9) with concentrated ammonium hydroxide. The resulting mixture is extracted with methylene chloride (2×50 ml). The combined extracts are dried (magnesium sulfate) and filtered. The filtrate is concentrated under reduced pressure to a solid which is dried in vacuo to yield 1.9 g (100% of 1. The NMR and mass spectrum are consistent with the structure. This compound is carried on to the next step.

B. (3β,5β,17β)-3-[[O-2,6-dideoxy-4-O-[1-(1-methyl-2-oxoethoxy)-3-oxopropyl]-β-D-ribo-hexopyranosyl-(1→4)-2,6-dideoxy-β-D-ribo-hexopyranosyl]oxy]androst-14-ene-17-carboxylic Acid Methyl Ester To a solution of compound 1 (1.9 g, 0.0012 mol) in 95:5 ethanol:water (100 ml) is added a solution of sodium periodate (1.9 g, 0.009 mol) in water (20 ml). The reaction is allowed to stir for 20 hrs at ambient temperature. The reaction is filtered and the filtrate is concentrated under reduced pressure to a solid. The solid is dissolved in water (100 ml) and extracted with methylene chloride (3×50 ml). The combined extracts are washed with 1% aqueous sodium bisulfate (1×50 ml), water (2×50 ml), dried (magnesium sulfate) and filtered. The filtrate is concentrated under reduced pressure to a foamy white solid which is dried in vacuo yielding 1.81 g (96%) of 2. This compound is carried on to the next step.

C. (3β,5β,17β)-3-[[O-2,6-dideoxy-4-O-[3-hydroxypropyl-1-(2-hydroxy-1-methylethoxy)]-β-D-ribo-hexopyranosyl-(1→4)-2,6-dideoxy-β-D-ribo-hexopyranosyl]oxy]androst-14-ene-17-carboxylic Acid Methyl Ester To a solution of 2 (1.81 g, 0.0025 mol) in 95:5 methanol:water (100 ml) is added sodium borohydride (0.94 g, 0.025 mol) and the solution is allowed to stir at ambient temperature for 1 hr. Acetic acid is added dropwise to the reaction to bring the pH to 7. The reaction is then concentrated under reduced pressure to a solid. The solid is dissolved in water (30 ml) and extracted with methylene chloride (3×25 ml), dried (magnesium sulfate) and filtered. The filtrate is concentrated under reduced pressure to a solid which is dried in vacuo to yield 1.31 g (72%) of 3. This compound is carried on to the next step.

D. (3β,5β,17β)-3-[(O-2,6-dideoxy-β-D-ribo-hexopyranosyl-(1→4)-2,6-dideoxy-β-D-ribo-hexopyranosyl)oxy]androst-14-ene-17-carboxylic Acid Methyl Ester To a solution of compound 3 (1.3 g, 0.0018 mol) in methanol (100 ml) is added 0.05N hydrochloric acid (22.1 ml). The reaction is allowed to stir at ambient temperature for 3 hrs. The reaction is then neutralized with saturated aqueous sodium bicarbonate solution and concentrated under reduced pressure to a solid. The solid is dissolved in water (50 ml) and extracted with methylene chloride (3×25 ml). The combined extracts are dried (magnesium sulfate) and filtered. The filtrate is concentrated under reduced pressure to a foamy solid which is dried in vacuo yielding 1.0 g (94%) of 4. This compound is carried on to the next step.

E. (3β,5β,17β)-3-[(O-3,4-Di-O-acetyl-2,6-dideoxy-β-D-ribohexopyranosyl-(1→4)-O-3-O-acetyl-2,6-dideoxy-β-D-ribo-hexopyranosyl)-oxy]androst-14-ene-17-carboxylic Acid Methyl Ester Compound 4 (1.0 g, 0.0017 mol) is dissolved in anhydrous pyridine (15 ml). Anhydrous acetic anhydride (15 ml) is added and the reaction is allowed to stir at 80° C. for 3 hrs, the reaction is then is gradually cooled to ambient temperature and stirred for 18 hrs. The reaction is poured into water (200 ml) and stirred for 10 min. The aqueous mixture is extracted with methylene chloride (2×75 ml). The combined extracts are washed with saturated aqueous sodium bicarbonate solution (3×100 ml), water (1×100 ml), dried (magnesium sulfate) and filtered. The filtrate is concentrated under reduced pressure to a foamy solid which is dried in vacuo to yield 0.78 g (64%) of 5. This compound is carried on to the next step.

F. (3β,5β,14β,15α,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl)oxy]-15-iodo-1→4-isocyanato-androstane-17-carboxylic Acid, Methyl Ester Compound 5 (0.76 g, 0.001 mol) is dissolved in ethyl acetate (4.5 ml) and acetonitrile (9 ml) and the solution is cooled to 1° C. in an ice/methanol bath. Silver cyanate (0.19 g, 0.0013 mol) is added followed by the dropwise addition of iodine (0.30 g, 0.0012 mol) in ethyl acetate (13.5 ml). Upon completion of the iodine addition (20 min) the reaction is allowed to continue stirring cold for an additional 1 hr. The reaction is then diluted with ethyl acetate (50 ml) and filtered through celite. The filtrate is washed with 1% aqueous sodium sulfite solution (1×50 ml) and the organic layer is then concentrated under reduced pressure to yield 0.9 g (9.6%) of 6 as a foamy solid. This compound is carried on to the next step.

G. (3β,5β,14β,17β)-3-[(O-3,4-Di-O-acetyl-2,6-dideoxy-β-D-ribo-hexopyranosyl-(1→4)-O-3-O-acetyl-2,6-dideoxy-β-D-ribo-hexopyranosyl)oxy]14-isocyanato-androstane-17-carboxylic Acid Methyl Ester In a flame-dried apparatus under a nitrogen atmosphere 6 is dissolved (0.9 g, 0.001 mol) in anhydrous methylene chloride (18 ml). To this solution is added catalytic 2,2'-azobisisobutyronitrile (AIBN, 0.001 g) followed by tributyltin hydride (0.3 ml, 0.32 g, 0.001 mol). The resulting solution is allowed to stir at ambient temperature for 3 hr then is concentrated under reduced pressure to an oil. The oil is triturated with hexanes to form a white solid which is collected by filtration and air dried to yield 0.65 g (84%) of 7. This compound is carried on to the next step.

H. (3β,5β,14β,17b)-3-[(O-3,4-Di-O-acetyl-2,6-dideoxy-β-D-ribo-hexopyranosyl-(1→4)-O-3O-acetyl-2,6-dideoxy-β-D-ribo-hexopyranosyl)oxy]-14 amino-androstane-17-carboxylic Acid, Methyl Ester To a suspension of compound 7 (0.65 g, 0.00085 mol) in acetonitrile (25 ml) is added a solution of potassium carbonate (1.8 g, 0.013 mol, 15 eq) in water (10 ml). The reaction is stirred at reflux temperature for 3 hrs. Upon cooling to room temperature, the reaction is concentrated under reduced pressure to remove the acetonitrile. To the remaining aqueous residue is added water (10 ml) and the mixture is acidified with 1N hydrochloric acid to a pH of 1, then quickly made basic (pH 9) with concentrated ammonium hydroxide. The aqueous mixture is extracted with methylene chloride (2×50 ml) and the combined layers are dried (magnesium sulfate) and filtered. The filtrate is concentrated under reduced pressure to a solid which is dried in vacuo to yield 0.6 g (96%) of crude 9. This compound is used directly in the next step.

I. (3β,5β,14β,17β)-14 Amino-3-[(O-2,6-dideoxy-β-D-ribo-hexopyranosyl-(1→4)-O-2,6-dideoxy-β-D-ribo-hexopyranosyl)oxy]androstane-17-carboxylic Acid, Methyl Ester In a flame-dried apparatus under a nitrogen atmosphere is dissolved compound 8 (0.60 g, 0.0082 mol) in anhydrous methanol (25 ml). A solution of sodium methoxide (0.35 g, 0.007 mol) in anhydrous methanol (10 ml) is added and the reaction is allowed to stir at ambient temperature for 1 hr. The reaction is then concentrated under reduced pressure to a white residue. The residue is dissolved in water (50 ml) and cooled in an ice/water bath. The solution is acidified with 1N hydrochloric acid to a pH of 1 then quickly made basic (pH 9) with concentrated ammonium hydroxide. The aqueous mixture is extracted with methylene chloride (3×25 ml). The combined extracts are dried (magnesium sulfate) and filtered. The filtrate is concentrated under reduced pressure to a solid. The solid is chromatographed on silica gel (230–400 mesh) using 9:1 methylene chloride:methanol containing 0.5% concentrated ammonium hydroxide as the eluent. Fractions containing the pure product are combined and concentrated under reduced pressure to a solid which is dried in vacuo to yield the (3β,5β,14β,17β,)-14-Amino-3-[(O-2,6-dideoxy-β-D-ribo-hexopyranosyl-(1→4)-O-2,6-dideoxy-β-D-ribo-hexo-pyranosyl)oxy]androstane-17-carboxylic acid, methyl ester Final Product.

EXAMPLE 3

(3β,5β,14β,17β)-14-Amino-3-hydroxy-androstane-17-carboxylic Acid Methyl Ester

A.

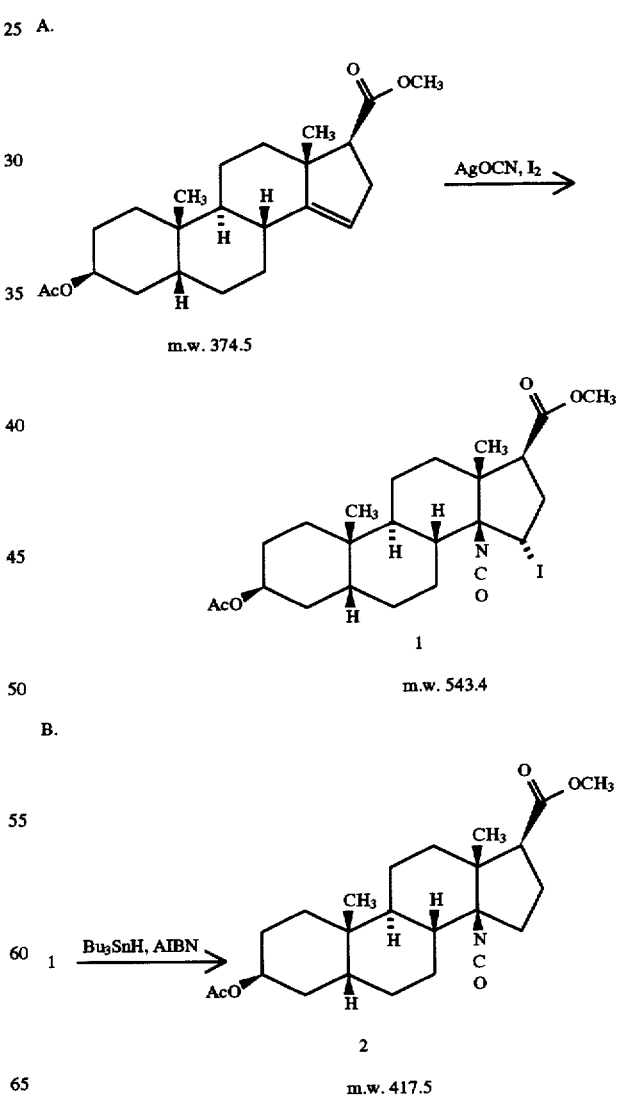

C.

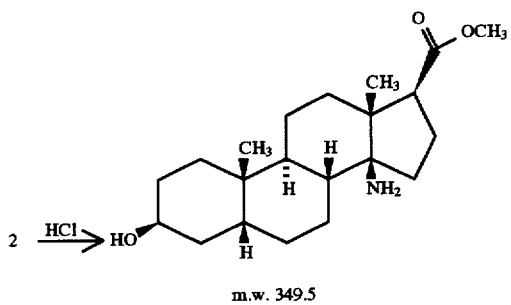

m.w. 349.5

A. (3β,5β,14β,15α,17β)-3-Acetyloxy-15-iodo-14-isocyanato-androstane-17-carboxylic Acid, Methyl Ester The preparation of (3β,5β,17β)-3-acetyloxy-androst-14-ene-17-carboxylic acid methyl ester is described in U.S. Pat. Nos. 4,855,280; 4,584,289; 4,325,879, incorporated by reference herein.

(3β,5β,17β)-3-Acetyloxy-androst-14-ene-17-carboxylic acid methyl ester (50 g, 0.134 mol) is dissolved in ethyl acetate (160 ml) and acetonitrile (320 ml) and the solution is cooled to 1° C. in an ice/methanol bath. Silver cyanate (23.7 g, 0.158 mol) is added followed by the dropwise addition of iodine (37.2 g, 0.147 mol) in ethyl acetate (480 ml). Upon completion of the iodine addition (20 min) the reaction is allowed to continue stirring cold for an additional 1 hr. The reaction is then filtered and—the filtrate is washed with 1% aqueous sodium sulfite solution (1×500 ml). The organic layer is then concentrated under reduced pressure to yield 70 g. (96%) of 1 as an oil. This compound is carried on to the next step.

B. (3β,5β,14β,17β)-3-Acetyloxy-14-isocyanato-androstane-17-carboxylic Acid Methyl Ester Compound 2 (65 g, 0.121 mol) is dissolved in methylene chloride (325 ml). To this solution is added catalytic 2,2'-azobisisobutyronitrile (AIBN, 0.005 g) followed by tributyltin hydride (33.3 ml, 36 g, 0.126 mol). The resulting solution is allowed to stir at 29° C. for 2.5 hr then is concentrated under reduced pressure to an oil. The oil is triturated with hexanes (350 ml) to form a white solid which is collected by filtration and air dried to yield 38.3 g (77%) of 2. This compound is carried on to the next step.

C. (3β,5β,14β,17β)-14-Amino-3-hydroxy-androstane-17-carboxylic Acid Methyl Ester Compound 2 is combined with acetonitrile (247 ml) and concentrated hydrochloric acid (133 ml) and stirred. After 3 hours, water (133 ml) is added and the reaction is allowed to continue stirring at ambient temperature for 48 hours. The reaction is then cooled in an ice/water bath to maintain a temperature below 25° C. while concentrated ammonium hydroxide is added dropwise to make the solution basic (pH-9). The resulting mixture is then extracted with methylene chloride (4×200 ml) and the combined extracts are washed with water (1×250 ml), dried (magnesium sulfate) and concentrated under reduced pressure to yield the (3β,5β,14β,17β)-14-amino-3-hydroxy-androstane-17-carboxylic acid methyl ester, final product.

Further, the 17-position carboxylic acid ester compounds prepared according to the iodoisocyanate chemistry, illustrated in Examples 1, 2, 3, hereinbefore, can be converted to the 17-position carboxamide derivatives as illustrated in Examples 4, 5, 6, and 7.

EXAMPLE 4

(3β,5β,14β,17β)-14-Amino-3-[(O-2,6-dideoxy-β-D-ribo-hexopyranosyl-(1→4)-O-2,6-dideoxy-β-D-ribo-hexopyranosyl)oxy]-N-methyl-androstane-17-carboxamide

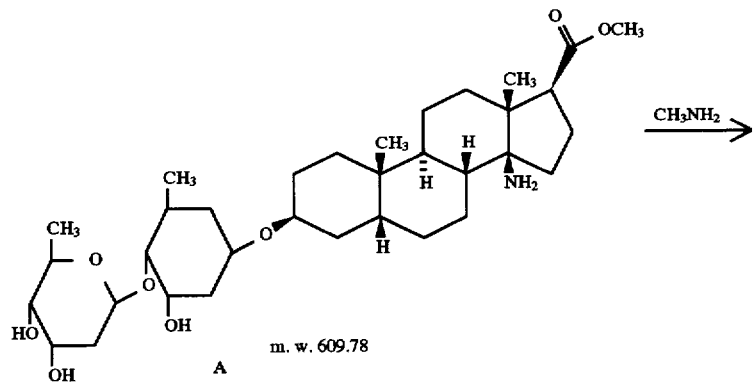

m. w. 609.78

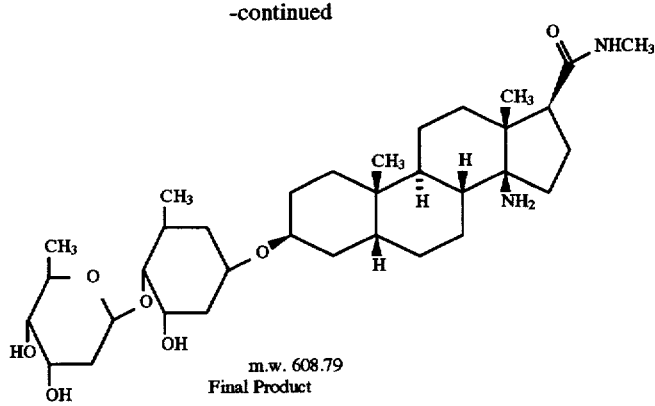

m.w. 608.79
Final Product

In a stainless steel bomb is dissolved, A., (3β,5β,14β,17β)-14-amino-3-[(O-2,6-dideoxy-b-D-ribo-hexopyranosyl-(1→4)-O-2,6-dideoxy-b-D-ribo-hexopyranosyl)oxy]androstane-17-carboxylic acid, methyl ester, (0.61 g, 0.001 mol) in methanol (15 ml) and the solution is cooled in a ice/water bath. Gaseous methylamine is then bubbled in to saturate the solution (15 min) and the reaction vessel is sealed and heated at 90° C. for 10 days. Upon cooling to ambient temperature, the reaction vessel is opened and the contents are concentrated under reduced pressure to a solid.

The solid is purified by silica gel chromatography using 80:20 methylene chloride:methanol containing 1% concentrated ammonium hydroxide as the eluent. Fractions containing the pure product are combined, concentrated under reduced pressure and dried in vacuo to give the pure product.

EXAMPLE 5

(3β,5β,14β,17β)-14-Amino-3-[(O-2,6-dideoxy-β-D-ribo-hexopyranosyl-(1→4)-O-2,6-dideoxy-β-D-ribo-hexopyranosyl)oxy]androstane-17-carboxamide

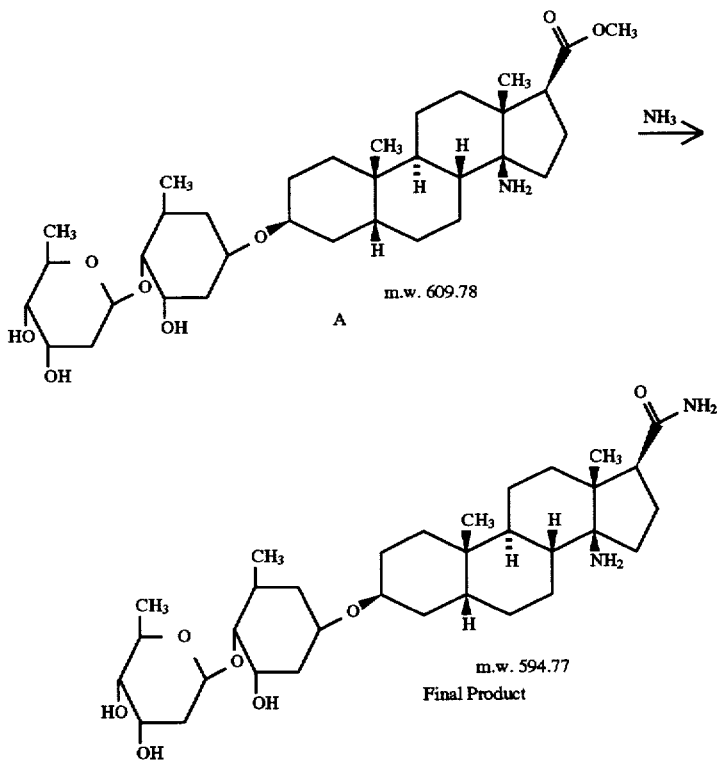

In a stainless steel bomb is dissolved, A., (3β,5β,14β,17β)-14-amino-3-[(O-2,6-dideoxy-b-D-ribo-hexopyranosyl-(1→4)-O-2,6-dideoxy-b-D-ribo-hexopyranosyl)oxy]androstane-17-carboxylic acid, methyl ester, (0.61 g, 0.001 mol) in methanol (15 ml) and the solution is cooled in a ice/water bath. Ammonia gas is then bubbled in to saturate the solution (15 min) and the reaction vessel is sealed and heated at 90° C. for 10 days. Upon cooling to ambient temperature, the reaction vessel is opened and the contents are concentrated under reduced pressure to a solid. The solid is purified by silica gel chromatography using 75:25 methylene chloride:methanol containing 1% concentrated ammonium hydroxide as the eluent. Fractions containing the pure product are combined, concentrated under reduced pressure and dried in vacuo to give the pure Final Product.

EXAMPLE 6

(3β,5β, 14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17-carboxamide

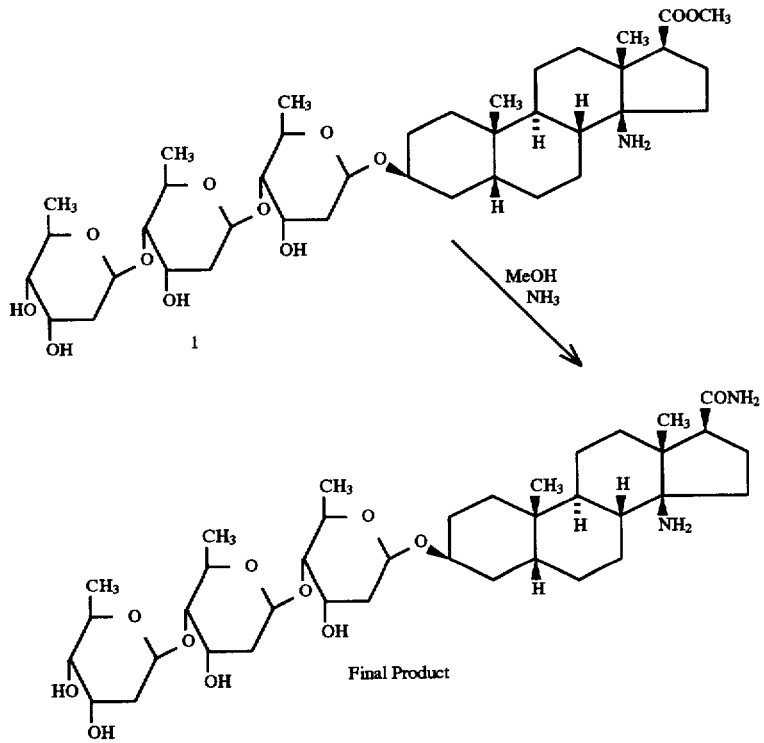

To a stainless steel bomb is added 298 mg (0.0004 mole) of 1. (3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-O-2,6-dideoxy-β-D-ribo-hexopyranosyl)oxy]androstane-17-carboxylic Acid, Methyl Ester and 10 ml MeOH, then bubble in NH₃ gas is bubbled in, while cooling in an ice/water bath, until saturated (15 min). The clear solution is sealed in the bomb and is heated at 90° C. for 10 days. If the reaction is complete, based on TLC, the light yellow reaction mixture is concentrated on the roto-evap, under reduced pressure, to yield an off-white solid residue. This material is purified by flash chromatography using the mobile phase of 25% MeOH/CH₂Cl₂+ NH₄OH. Fractions are collected and monitored by TLC.

Based on TLC, combined fractions (43–81) showing one spot on TLC at Rf0.23, are concentrated on the roto-evap, under reduced pressure to yield an off-white solid. This solid is dried in-vacuo at 55° C. overnight to yield the pure final product.

EXAMPLE 7

(3β,5β,14β,17β)-14-Amino-3-[(O-2,6-dideoxy-β-D-ribo-hexopyranosyl-(1→4)-O-2,6-dideoxy-β-D-ribo-hexopyranosyl(1→4)-2,6-dideoxy-β-D-ribo-hexopyranosyl)oxy]-N-methylandrostane-17-carboxamide

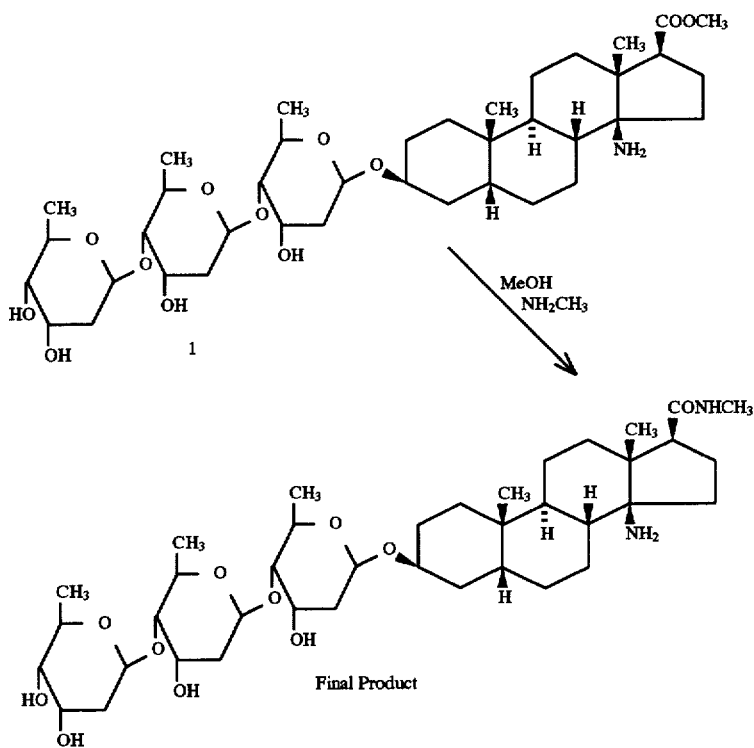

To a stainless steel bomb is added 298 mg (0.0004 mole) of 1. (3β,5β,14β,17β)-14-Amino-3-[(O-2,6-dideoxy-β-D-ribo-hexo-pyranosyl-(1→4)-O-2,6-dideoxy-β-D-ribo-hexopyranosyl-(1→4)-2,6-dideoxy-β-D-ribo-hexopyranosyl)oxy]androstane-17-carboxylic Acid, Methyl Ester and 10 ml MeOH, then methylamine is bubbled in, while cooling in an ice/water bath, until saturated ~15 min. The clear solution is sealed in the bomb and heated at 90° C. for 10 days.

The bomb is removed from the oven, cooled, opened and checked by TLC. If the TLC shows no starting material, the light yellow reaction mixture is concentrated on a roto-evap, under reduced pressure, to yield a semi-solid residue. This semi-solid residue is purified by flash chromatography using a mobile phase of 20% MeOH/CH$_2$Cl$_2$+NH$_4$OH. (Initial ratio: 20/80/0.9; final ratio 20/80/1.8). Based on TLC, combined fractions 22–98 showing one spot on TLC at Rf0.43 (20% MeOH/CH$_2$Cl$_2$+NH$_4$OH), are concentrated on a roto-evap, under reduced pressure to yield an off-white solid. This solid is triturated with cold ether and collected by filtration to yield the off-white solid final product, which is dried, in-vacuo at 55° C. for 48 hr to yield the pure final product.

The novel compounds of the present invention are also prepared according to the chemistry described in the prior art, U.S. Pat. Nos. 4,325,879; 4,552,868; 4,552,868; 4,584,289; and 4,885,280, incorporated by reference herein. The following non-limiting examples are illustrative of how the compounds of the present invention can be prepared according to the prior art.

EXAMPLE 8

(3β,5β,14β,17β)-14-Amino-3-[[O-2,6-dideoxy-β-D-ribo-hexopyranosyl-(1→4)-6-deoxy-2,3-O-(1-methylethylidene)-α-L-mannopyranosyl]-oxy] androstane-17-carboxylic acid, methyl ester

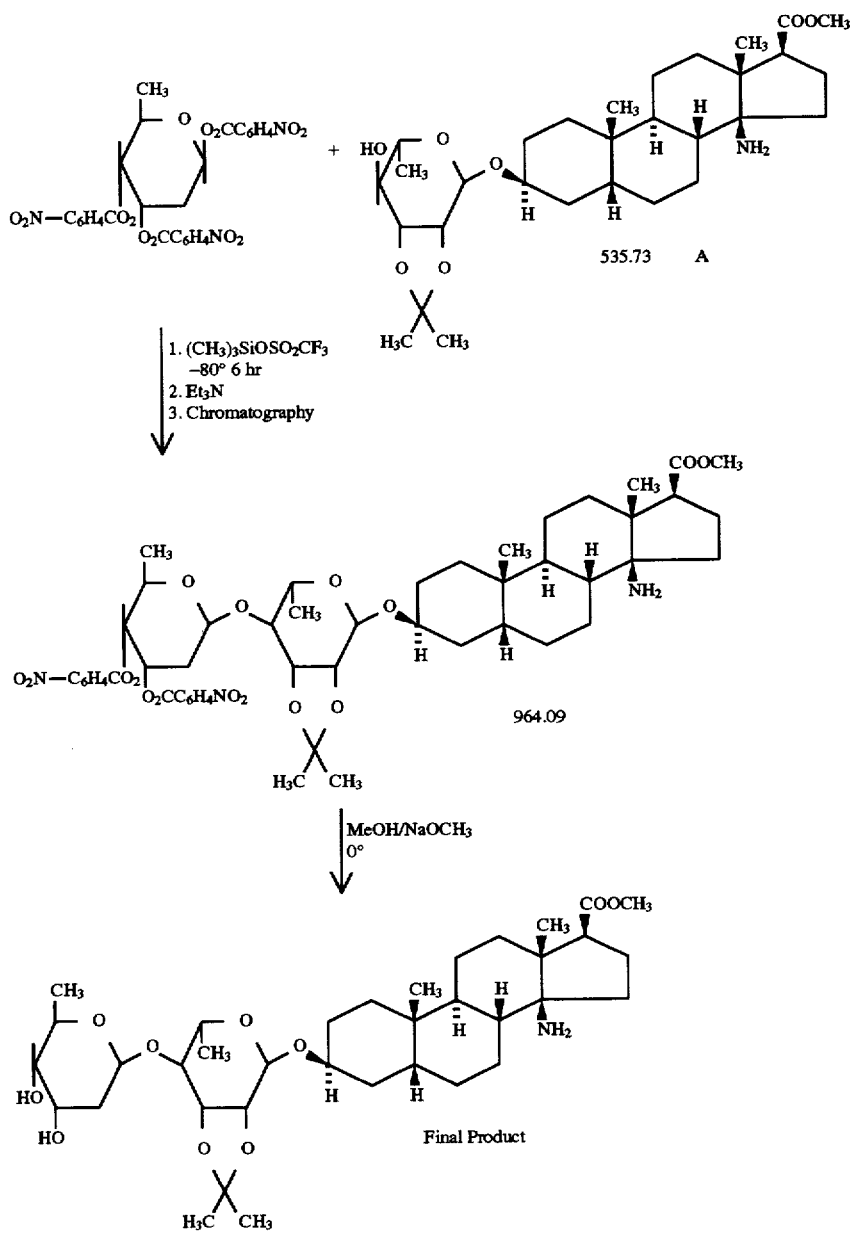

To a mixture of 1.125 g (2.1 mmoles) of, A., (3β,5β,14β, 17β)-14-Amino-3-[[6-deoxy-2,3-O-(1-methylethylidene)-α-L-mannopyranosyl]oxy]androstane-17-carboxylic acid, methyl ester, prepared according to the procedure described in U.S. Pat. No. 4,885,280, incorporated by reference herein, and 1.250 g (2.1 mmoles) of 2,6-Dideoxy-1,3,4-D-(4-nitrobenzoyl)-D-ribohexanopyranoside in 60 ml of $CH_2Cl_2$ is added 3.0 g of molecular sieves, 4A°, 8–12 mesh. The mixture is stirred at room temperature for 15 min then cooled in a dry ice/acetone bath; and then 2.0 ml of trimethylsilyl trifluoromethanesulfonate (Lancaster), in 10.0 ml of $CH_2Cl_2$, is added dropwise. After the mixture is stirred at ca. −80° for 6 hr, 8.0 ml of triethylamine is added to the cold mixture and stirring continues for 10 min. The mixture is allowed to slowly warm in the refrigerator overnight.

The solvent is removed in vacuo and the residue chromatographed on silica. Contaminating materials are eluted with $CH_2Cl_2$, then the desired fraction is eluted with EtOAc/$CH_2Cl_2$ (1:4) to yield 1.9.8 g.

To a solution of 400 mg (0.415 mmoles) of the above p-nitrobenzoylated disaccharide, in 1.0 ml of dry methanol (Aldrich, anhydrous) is added via syringe 7.2 ml of 0.1217 mM $NaOCH_3$ in dry methanol (Aldrich). The mixture is stirred at 0° for 6 hr and the resulting product precipitates from the reaction mixture to yield the Final Product (3β,5β, 14β,17β)-14-Amino-3-[[O-2,6-dideoxy-β-D-ribo-hexopyranosyl-(1→4)-6-deoxy-2,3-O-(1-methylethylidene)-a-L-mannopyranosyl]oxy]androstane-17-carboxylic acid, methyl ester.

EXAMPLE 9

14β-amino-3β-[α-(L)-rhamnopyranosyloxy-(1→4)-2',3'-O-isopropylidene-α-(L)-rhamnopyranosyloxy]-5β-androstane-17β-carboxylic acid, methyl ester

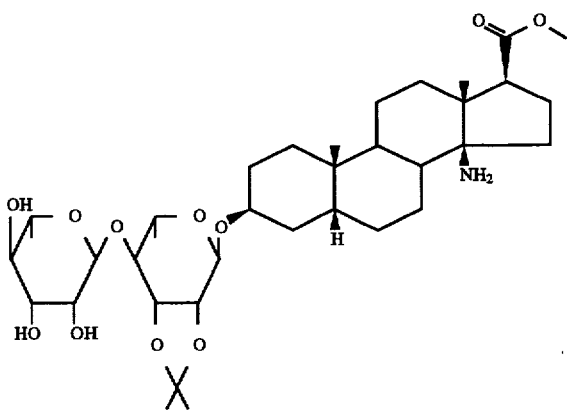

260 mg of 14β-azido-3β-[2',3'-O-isopropylidene-α-(L)-rhamnopyranosyloxy]-5β-androstane-17β-carboxylic acid, methyl ester, prepared according to the procedures described in U.S. Pat. Nos. 4,885,280 and 4,325,879, incorporated by reference herein, are dissolved in 12 ml of acetonitrile, and the solution is stirred for 15 minutes, in the presence of a molecular sieve (130 mg, 3 A), and 325 mg of tri-O-acetyl-rhamnosyl bromide. 232 mg of mercury cyanide are added and the reaction mixture is stirred for 3 hours at room temperature.

After addition of a saturated solution of sodium bicarbonate, filtration, extraction with toluene, and purification by chromatography on silica gel column under pressure (500 mb), eluting with a ethyl acetate/hexane mixture (1:2), 252 mg 14β-azido-3β-[tri-2",3",4"-O-acetate-α-(L)-rhamnopyranosyloxy]-(1→4)-2',3'-O-isopropylidene-α-(L)-rhamnopyranosyloxy]-5β-androstane-17β-carboxylic acid, methyl ester, are obtained.

This di-rhamnosyl-14-azido derivative can be crystallized in a ethyl ether/petroleum ether mixture.

A mixture of 8.5 ml of absolute ethyl alcohol deoxygenated by argon, 99.5 mg of tellurium powder and 74 mg of sodium borohydride, containing 250 mg of the above di-rhamnosyl 14-azido derivative is stirred for 24 hours at room temperature.

After filtration on Celite, evaporation, extraction with ethyl acetate, and washing with water, the residue is purified by chromatography under pressure on a silica column, eluting with a chloroform/ethyl alcohol/ammonium hydroxide (89:10:1) mixture to yield 14β-amino-3β-[α-(L)-rhamnopyranosyloxy-(1→4)-2',3'-O-isopropylidenedene-β-α-(L)-rhamnopyranosyloxy]-5β-androstane-17β-carboxylic acid, methyl ester.

EXAMPLE 10

14β-amino-3β-[tri-2",3",4"-O-acetyl-α-(L)-rhamnopyranosyloxy-(1→4)-2',3'-O-isopropylidene-α-(L)-rhamnopyranosyloxy]-5β-androstane-17β-carboxylic acid, methyl ester

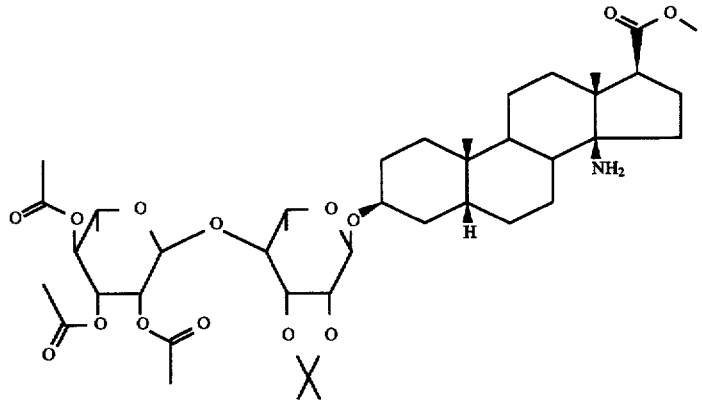

5.0 g of the tri-hydroxy derivative obtained as indicated in Example 8, are dissolved in 37 ml of methylene chloride and the solution is cooled on an ice bath. Acetyl anhydride (2.4 ml) and dimethylaminopyridine (313 mg) are added to the solution and the reaction mixture is stirred overnight at room temperature.

An aqueous solution of sodium hydroxide is poured into the reaction mixture, and stirring is continued for 5 minutes, followed by an extraction with methylene chloride.

The organic phases are washed with $H_2O+NH_4OH$, dried over $Na_2SO_4$ and evaporated until dry. The crude triacetylated product thus obtained is purified by flash chromatography on silica column, eluting with a methylene chloride/methyl alcohol/ammonium hydroxide mixture (97:2.7:0.27), to yield 14β-amino-3β-[tri-2",3",4"-O-acetyl-α-(L)-rhamnopyranosyloxy-(1→4)-2',3'-O-isopropylidene-α-(L)-rhamnopyranosyloxy]-5β-androstane-17β-carboxylic acid, methyl ester.

EXAMPLE 11

14β-amino-3β-[2",3"-O-isopropylidene-α-(L)-rhamnopyranosyloxy-(1→4)-2',3'-O-isopropylidene-α-(L)-rhamnopyranosyloxy]]-5β-androstane-17β-carboxylic acid, methyl ester

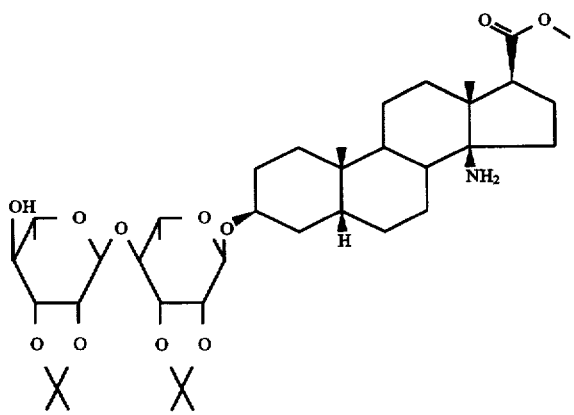

To a solution of 11.2 g of the tri-hydroxy derivative, obtained as described in Example 8, in 77 ml of acetone, 97 ml of dimethoxypropane and 3.5 g of p-toluene sulfonic acid·H$_2$O are added. The reaction mixture is stirred at room temperature for 1 hour and an aqueous solution of sodium hydroxide is poured into the reaction mixture with stirring for a few minutes, followed by an extraction with a methylene chloride/methyl alcohol mixture.

The organic phases are washed with H$_2$O+NH$_4$OH, dried over Na$_2$SO$_4$ and evaporated until dry. The crude product thus obtained is purified by crystallization in isopropyl ether to yield 14β-amino-3β-[2",3"-isopropylidene-α-(L)-rhamnopyranosyloxy(1→4)-2',3'-O-isopropylidene-α-(L)-rhamnopyranosyloxy]]-5β-androstane-β17β-carboxylic acid, methyl ester.

EXAMPLE 12

14β-amino-3β-[α-(L)-rhamnopyranosyloxy-(1→4)-α-(L)-rhamnopyranosyloxy]-5β-androstane-17β-carboxylic acid, methyl ester

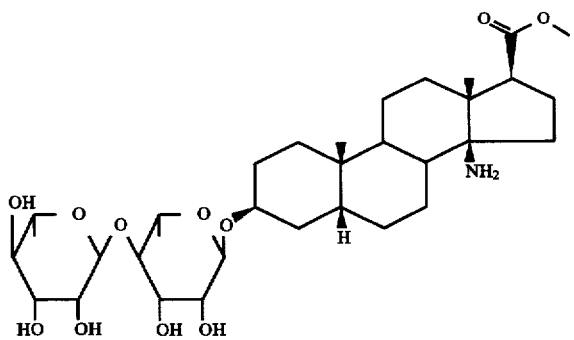

The tri-hydroxy derivative obtained as described in Example 8 (103 mg) is dissolved in 2 ml of chloroform in the presence of 0.2 ml of trifluoroacetic acid and some water (1%). The reaction is carried out at room temperature for 1 hour.

After extraction with a methylene chloride/methyl alcohol mixture (85:15), washing with a saturated hydrogencarbonate solution, with water, and evaporation until dry, the residue is purified by chromatography on a silica column under pressure, eluting with a methylene chloride/methyl alcohol/ammonium hydroxide mixture (84:15:1), to yield the 14β-amino-3β-[α-(L)-rhamnopyranosyloxy-(1→4)-α-(L)-rhamnopyranosyloxy]-5β-androstane-17β-carboxylic acid, methyl ester.

Assessment of Pharmacological Activity

It is postulated that the positive inotropic effect of a cardiotonic steroid compound is due to its effect on the Na$^+$, K$^+$pump in the sarcolemma of the cardiac muscle cells. Specifically, the cardiotonic steroids inhibit the Na$^+$, K$^+$-activated adenosine triphosphatase which in turn leads to an increase in intracellular calcium. Thus, more calcium is available to activate the contractile mechanism. See generally, Goodman and Gilman, *The Pharmacological Basis of Therapeutics*, Chapter 34 (8th Ed., 1990).

The positive inotropic activity of a new chemical entity is assessed both in isolated cardiac tissues and in whole animal models. The isolated tissue provides a direct measurement of the inotropic potential of a compound as the system is virtually free from metabolic, neurohormonal and absorption interferences which may influence the tissue response. The in vivo assays provide an assessment which takes into account those physiological parameters lacking in the isolated tissue assay.

In the assay for inotropic activity, papillary muscle strips from guinea pig hearts are utilized. Although the papillary muscle is involved more with valve function, the basic contractile response exhibited by this muscle is similar to that of ventricular muscle. For the assay, a segment of papillary muscle dissected from a guinea pig heart is suspended in an organ bath which provides the tissue with a temperature controlled, aqueous environment containing the substrates necessary for cellular function. By attaching a force transducer to the free end of the muscle strip such that the muscle is suspended between a fixed base and the transducer and applying an electrical stimulus, it is possible to measure shortening or contraction in response to various concentrations of test compounds. Under typical conditions, positive inotropy is defined as the increase in contractile force elicited by an unknown agent and the data is usually reported as the concentration of drug necessary to elicit a 50% increase in contracile force from baseline (EC$_{50}$).

The assessment of positive inotropy in vivo is made in two ways. The first is very similar to the measurement described for the in vivo method in that a strain gauge is sutured to the exterior of the heart to determine contractile force. In the second protocol, a force transducer is inserted into the left ventricle to detect pressure changes. The myocardial contractile force is correlated to the rate of pressure development within the left ventricle and is expressed as +dP/dt. In either case, the data is reported as the amount of drug necessary to achieve a level of activity such as 30% increase in contractility or +dP/dt (i.e., ED$_{30}$) and is expressed as mg drug/kg weight of the animal.

Pharmaceutical Compositions

The novel oligosaccharide-containing 14-aminosteroid compounds of the present invention may be administered to humans or other mammals by a variety of routes, including, but not limited to, oral dosage forms and injections (intravenous, intramuscular, intraperitoneal and subcutaneous). Numerous other dosage forms containing the novel oligosaccharide-containing 14-aminosteroid compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the oligosaccharide-containing 14-aminosteroid compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular oligosaccharide-containing 14-aminosteroid compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in Remington's Pharmaceutical Sciences, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in Handbook of Pharmaceutical Excipients, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl parebon and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropyl methylcellulose, methylcellulose, sugar solutions, such as sucrose and sorbitol, and ethylcellulose. The compositions of the present invention include 1–10% binders.

Compounds of the present invention may comprise from about 0.1% to about 99.9% by weight of the pharmaceutical compositions of the present invention. Preferably the compounds of the present invention comprise from about 20% to about 80% by weight of the pharmaceutical compositions of the present invention.

Accordingly, the pharmaceutical compositions of the present invention include from 15–95% of an oligosaccharide-containing 14-aminosteroid compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein. It is well within the capabilities of one skilled in the art to vary the non-limiting examples described herein to achieve a broad range of pharmaceutical compositions.

The choice of a pharmaceutically-acceptable excipient to be used in conjunction with the oligosaccharide-containing 14-aminosteroid compounds of the present invention is basically determined by the way the compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The preferred mode of administering the oligosaccharide-containing 14-aminosteroid compounds of the present invention is orally. The preferred unit dosage form is therefore tablets, capsules and the like, comprising a safe and effective amount of the oligosaccharide-containing 14-aminosteroid compounds of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

Various oral dosage forms can be used, including such solid forms as tablets, capsules, granules and bulk powders. These oral dosage forms comprise a safe and effective amount, preferably from 0.25 mg to 5.0 mg, of the oligosaccharide-containing 14-aminosteroid. More preferably these oral dosage forms comprise 0.5 mg to 1.0 mg of the oligosaccharide-containing 14-aminosteroid. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spread tissue the composition on the epidermal or epithelial tissue of the subject. Such compositions include, for example, lotions, creams, solutions, gels and solids. These topical compositions comprise a safe and effective amount, preferably from about 0.5 mg to 2.0 mg, of the oligosaccharide-containing 14-aminosteroid. More preferably these topical compositions comprise 1.0 mg of the oligosaccharides-containing 14-aminosteroid. Suitable carriers for topical administration preferably remain in place on the skin as a continuous film, and resist being removed by perspiration or immersion in water. Generally, the carrier is organic in nature and capable of having dispersed or dissolved therein the oligosaccharide-containing 14-aminosteroid. The carrier may include pharmaceutically-acceptable emolients, emulsifiers, thickening agents, and solvents.

The compositions of this invention can also be administered via the inhalation route. Such compositions are prepared in a matrix comprising a solvent such as water or a glycol, preservatives such as methyl or propyl paraben and propellants such as nitrogen or carbon dioxide.

Additionally, the compositions of this invention can be administered via a subcutaneous implant formed from silicone elastomers, ethylene vinyl acetate co-polymers or lactic-glycolic co-polymers.

In order to illustrate how to prepare pharmaceutical compositions containing the novel compounds of the present invention, the following non-limiting pharmaceutical composition examples are provided.

PHARMACEUTICAL COMPOSITION EXAMPLES

Example 1

An immediate release oral dosage form (tablet) containing the (3β,5β,14β,17β)-14-Amino-3-[(O-2,6-dideoxy-β-D-ribo-hexopyranosyl-(1→4)-O-2,6-dideoxy-β-D-ribo-hexopyranosyl(1→4)-2,6-dideoxy-β-D-ribo-hexopyranosyl)oxy]—N-methylandrostane-17-carboxamide has the following composition:

| Active Ingredient | Amount |
|---|---|
| (3β,5β,14β,17β)-14-Amino-3-[(O-2,6-dideoxy-β-D-ribo-hexopyranosyl-(1→4)-O-2,6-dideoxy-β-D-ribo-hexopyranosyl(1→4)-2,6-dideoxy-β-D-ribo-hexopyranosyl)oxy]-N-methylandrostane-17-carboxamide | 1.0 mg |

-continued

| Active Ingredient | Amount |
|---|---|
| Excipients | |
| Microcrystalline cellulose | 28.5 mg |
| Lactose, hydrous | 67.2 mg |
| Crospovidone | 3.0 mg |
| Magnesium stearate | 0.3 mg |

Manufacturing Directions: (for 10,000 tablets).

1) 10.0 g of the drug, 285.0 g of microcrystalline cellulose, 672.0 g of lactose and 30.0 g of crospovidone are mixed in a Patterson-Kelley (PK) or other suitable blender, 2) the above mixture is blended with 3.0 g of magnesium stearate in a PK or suitable blender, 3) the above final blend is compacted into 100.0 mg tablets on a suitable tableting machine.

Example 2

A parenteral dosage form containing the (3β,5β,14β,17β)-14-Amino-3-[[O-2,6-dideoxy-β-D-ribo-hexopyranosyl-(1→4)-6-deoxy-2,3-O-(1-methylethylidene)-α-L-mannopyranosyl]oxy]androstane-17-carboxylic acid, methyl ester; and suitable for use as an intravenous (I.V.) injection has the following composition:

| Active Ingredient | Amount |
|---|---|
| (3β,5β,14β,17β)-14-Amino-3-[[O-2,6-dideoxy-β-D-ribo-hexopyranosyl-(1→4)-6-deoxy-2,3-O-(1-methylethylidene)-α-L-mannopyranosyl]oxy]androstane-17-carboxylic acid | 1.0 mg |
| Excipients | |
| Mannitol | 200.0 mg |
| Citric acid/sodium citrate | quantity sufficient to adjust the pH between 5.5–6.5 |

Manufacturing directions: (for 1000 vials)

1) 1.0 g of the drug, 200.0 g of mannitol and sufficient sodium citrate and citric acid are dissolved in 2200.0 ml of sterile, deionized water for injection, 2) the above solution is filtered through a 0.22 micron sterile membrane filter, 3) 2.2 ml of the above sterile solution is filled into Type I glass vials and then lyophilized in a suitable lyophilizer, 4) the vials, after lyophilization, are stoppered with bromobutyl or other suitable stoppers and sealed. The lyophilized product is reconstituted with 2.0 ml of sterile water for injection immediately prior to use.

Example 3

A sustained release oral dosage form (tablet) containing the (3β,5β,14β, 17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17β-carboxamide has the following composition:

| Active Ingredient | Amount |
|---|---|
| (3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17-carboxamide | 5.0 mg |
| Excipients | |
| Hydroxypropylmethylcellulose | 120.0 mg |
| Lactose, hydrous | 120.0 mg |
| Magnesium stearate | 12.0 mg |
| Colloidal silicon dioxide | 4.0 mg |

Manufacturing Directions: (for 10,000 tablets)

1) 50.0 gm of the drug, 1.2 kg of hydroxypropylmethyl-cellulose and 1.2 kg of lactose are mixed intimately in a twin shell Patterson-Kelley or suitable mixer, 2) to the above mix are added 120 gm of magnesium stearate and 40 gm of colloidal silicon dioxide and this is lightly blended in a suitable mixer, 3) the above blend is compacted into tablets weighing 261.0 mg on a suitable tablet press.

Miscellaneous Examples

In addition to the above three examples, the drug active ingredient is formulated into a number of different dosage forms:

1) a pharmaceutical aerosol containing solvent (e.g. water, glycols), preservatives (methyl or propyl parabens) and propellants (nitrogen, carbon dioxide) or other suitable excipients, 2) a rectal suppository containing theobroma oil or polyethylene glycols, 3) a subcutaneous implant containing silicone elastomers, ethylene-vinyl acetate copolymers, lactic-glycolic copolymers and hydrogels or other suitable polymers, 4) commercially available implantable devices, 5) a transdermal system containing silicone fluid in an ethylene-vinyl acetate copolymer membrane or other suitable ingredients for delivery with or without the aid of iontophoresis, 6) a buccal mucoadhesive patch containing hydrocolloid polymers (hydroxyethyl cellulose, hydroxy-propyl cellulose, povidone) and other suitable polymers.

Methods of Treatment

The term. Congestive Heart Failure ("CHF") as used herein, denotes a progressive disease wherein the hemodynamic capacity as well as the structural integrity of the heart itself is increasingly and irreversibly compromised. The progression of CHF according to the patient's symptoms has been classified into four functional classifications by the New York Heart Association (NYHA).

New York Heart Association Functional Classification

Class

I. Patients with cardiac disease but without resulting limitations of physical activity. Ordinary physical activity does not cause undue fatigue, palpitation, dyspnea, or anginal pain.

II. Patients with cardiac disease resulting in slight limitation of physical activity. They are comfortable at rest. Ordinary physical activity results in fatigue, palpitation, dyspnea, or anginal pain.

III. Patients with cardiac disease resulting in marked limitation of physical activity. They are comfortable at rest. Less than ordinary physical activity causes fatigue, palpitation, dyspnea, or anginal pain.

IV. Patient with cardiac disease resulting in inability to carry on any physical activity without discomfort. Symptoms of cardiac insufficiency or of the anginal syndrome may be present even at rest. If any physical activity is undertaken, discomfort is increased.

NYHA Classes III and IV, also referred to as overt congestive heart failure, are often treated by administering compounds that increase cardiac contractility by exerting a positive inotropic effect. The reference compound for increasing cardiac contractility is oral digoxin. Treating the symptoms of the overt CHF by administering inotropes to increase CO to meet the metabolic needs of the body can improve the quality of life for a CHF patient because the heart can better supply the metabolic need of the body. Conventional wisdom, however, indicates that an inotrope, such as digitalis, might increase mortality rates because the inotropic action creates an extra work load for the heart. Furthermore, digitalis has a narrow therapeutic:toxic dose ratio and administration of digitalis at an earlier than Class III NYHA functional classification may not be prudent.

Additionally, the bipyridine inotrope, Milrinone, has been shown to aggravate ventricular arrhythmias and possibly increase mortality. See DiBianco, R., et al. "A Comparison of Oral Milrinone, Digoxin, and Their Combination in the Treatment of Patients with Chronic Heart Failure", *N. Engl. J. Med.* 320:677 (1989).

The term "hemodynamic" as used herein, refers to the mechanical capability of the heart. The initial hemodynamic consequence of heart failure is a decrease in stroke volume which is a measurement of the amount of blood ejected with each heart beat. The heart then compensates to increase the CO to maintain flow to the vital organs. As the heart failure worsens, intracardiac filling pressures are elevated as well as pulmonary and venous pressures. The heart is increasingly unable to supply the required CO.

The term "structural damage" as used herein, refers to the microscopic and macroscopic changes in the heart of a person suffering from CHF. Structurally, on a microscopic level the following changes occur: The early stage of cardiac hypertrophy is characterized morphologically by increases in the size of myofibrils and mitochondria as well as enlargement of mitochondria and nuclei. Muscle cells are larger than normal, but cellular organization is largely preserved. At a more advanced stage of hypertrophy, preferential increases in the size or number of specific organelles, such as mitochondria, as well as irregular addition of new contractile elements in localized areas of the cell, result in subtle abnormalities of cellular organization and contour. Adjacent cells may vary in their degree of enlargement.

Cells subjected to long-standing hypertrophy show more obvious disruptions in cellular organization, such as markedly enlarged nuclei with highly lobulated membranes, which displace adjacent myofibrils and cause breakdown of normal Z-band registration. The early preferential increase in mitochondria is supplanted by a predominance by volume of myofibrils. The late stage of hypertrophy is characterized by cell death and a loss of contractile elements with marked disruption of Z bands, severe disruption of the normal parallel arrangement of the sarcomeres, dilation and increased tortuosity of T tubules, and replacement of the contractile elements with fibrosis tissue. See Braunwald, *Heart Disease: A Textbook of Cardiovascular Medicine*, Vol. 1 (3rd ed. 1988). These microscopic changes are revealed on a macroscopic level by cardiac hypertrophy or enlargement of the heart. The hypertrophying heart becomes less efficient due to microscopic changes causing loss of contractile elements and fibrotic deposition and the patient's clinical symptoms worsen as he progresses through each NYHA functional classification.

The compounds of the present invention increase cardiac contractility. The dosage range can be between 0.001 mg and 5 mg/kg per day as determined by the attending physician according to the mode of administration, the severity of the CHF and the duration of treatment.

In order to illustrate the particular utility of these novel oligosaccharide-containing 14-aminosteroid compounds, for the treatment of CHF, the following non-limiting clinical examples are presented.

CLINICAL EXAMPLES

Example 1

An obese 65 year old white female with a 20 year history of non-insulin dependent diabetes mellitus and hypertension, and a myocardial infarction 2 years prior, is admitted to the coronary care unit after 12 hours of symptoms with an acute inferior myocardial infarction. Her hospital course is complicated by acute pulmonary edema which manifests itself by severe dyspnea at rest, orthopnea, jugular venous distention, bilateral rales to mid-scapula; a dilated heart and bilateral infiltrates on CXR. Her pulmonary capillary wedge pressure is 35 mmHg. She is treated with morphine, oxygen, intravenous nitroglycerin, a loop diuretic and 0.25 mg of (3β,5β,14β,17β]-14-Amino-3-[(O-2,6-dideoxy-β-D-ribo-hexopyranosyl-(1→4)-O-2,6-dideoxy-β-D-ribo-hexopyranosyl(1→4)-2,6-dideoxy-β-D-ribo-hexopyranosyl)oxy]-N-methyl-androstane-17β-carboxamide intravenously every 4 hours for three days, followed by 0.25 mg of (3β,5β,14β,17β]-14-Amino-3-[(O-2,6-dideoxy-β-D-ribo-hexopyranosyl-(1→4)-O-2,6-dideoxy-β-D-ribo-hexopyranosyl(1→4)-2,6-dideoxy-β-D-ribo-hexopyranosyl)oxy]—N-methyl-androstane-17β-carboxamide orally once a day. She improves on this regimen and is discharged in 10 days with dyspnea on mild exertion (mild congestive heart failure, NYHA Class II) to be followed as an outpatient on a diuretic, ACE inhibitor, nitroglycerin and 0.25 mg orally of (3β,5β,14β,17β]-14-Amino-3-[(O-2,6-dideoxy-β-D-ribo-hexopyranosyl-(1→4)-O-2,6-dideoxy-β-D-ribo-hexopyranosyl(1→4)-2,6-dideoxy-β-D-ribo-hexopyranosyl)oxy]-N-methylandrostane-17-carboxamide per day.

Example 2

A 44-year old black male with a history of long-standing uncontrolled hypertension and a one year history of moderate (NYHA Class III) congestive heart failure presents with several episodes of presyncope over the preceding 2 weeks. He also complains of fatigue and dyspnea when getting dressed. Medications include digoxin (0.25 mg/day), lasix and ACE inhibitor. He has an S3 gallop, pitting ankle edema, left ventricular hypertrophy and occasional PVCs on ECG. Additional evaluation discloses frequent multifocal ventricular ectopy and a run of non-sustained ventricular tachycardia on Holter monitoring, an ejection fraction of 30% by radionuclide ventriculography and a serum digoxin level of 2.2 ng/ml. The arrhythmias and pre-syncope are suspected to be a result of digitalis toxicity, and the drug is discontinued. (3β,5β,14β,17β]-14-Amino-3-[[O-2,6- dideoxy-β-D-ribo-hexopyranosyl-(1→4)-6-deoxy-2,3-O-(1-methylethylidene)-α-L-mannopyranosyl]oxy]androstane-17β-carboxylic acid, methyl ester is instituted at an oral dose of 0.25 mg per day. Because of persistence of fatigue and dyspnea, the dose is increased over the next six weeks to 1 mg daily with no additional episodes of presyncope, a reduction of PVCs and absence of nonsustained ventricular tachycardia on repeat Holter and an increase in the ejection fraction to 38%. His dyspnea with self-care activities such as dressing is resolved and he is able to work in his garden with mild occasional dyspnea (NYHA Class II). At one year follow-up his condition is unchanged.

Example 3

A 24 year-old previously healthy Chinese female presents with a two month history of dyspnea with strenuous exertion. There is no family history of heart disease; she is a non-smoker, and does not drink alcohol. Physical exam is normal with the exception of tachycardia and a laterally displaced point of maximum impulse. A heart rate of 105 and non-specific T wave flattening are seen on ECG, and CXR reveals an enlarged heart. Echocardiogram shows biventricular enlargement with global hypokinesia, and an ejection fraction of 40%. The valves appear normal. A symptom limited treadmill exercise test shows no evidence of ischemia. A diagnosis of idiopathic dilated cardiomyopathy, NYHA Class I, is made. Initial treatment with an ACE inhibitor produces an intolerable cough, and is therefore discontinued. (3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17β-carboxamide is administered orally at a dosage of 1 mg twice a day, and over the next month her ability to exercise improves. There is also an increase in the ejection fraction (by echocardiogram) to 55%, and an increase in exercise time of 200 seconds on the treadmill exercise test.

Example 4

A 55 year old white male with a history of two previous myocardial infarctions and whose father died suddenly at age 50, is being maintained on isosorbide dinitrate and a beta blocker with stable effort angina for two years. Over the preceding month, however, he develops dyspnea on walking up one flight of stairs, swelling of the ankles at night and occasional paroxysmal nocturnal dyspnea.

He has a resting heart rate of 90, 1+ pitting edema of the ankles, an S3 gallop, an enlarged heart and Kerly B lines on CXR. A diagnosis of mild (NYHA Class II) congestive heart failure due to ischemic heart disease is made. His beta blocker is discontinued by gradual tapering, and an ACE inhibitor and diuretic added, but on this new regimen his congestive heart failure worsens. (3β,5β,14β,17β)-14-Amino-3-[(O-2,6-dideoxy-β-D-ribo-hexopyranosyl)-(1→4)-2,6-dideoxy-β-D-ribo-hexopyranosyl)oxy]androstane-17β-carboxylic acid, methyl ester is orally administered at a dose of 4 mg once daily. His dyspnea and edema resolves (NYHA Class I), heart rate decreased to 75, S3 disappeared, heart size decreases and congestion on CXR resolves. There is an increase in exercise time of 170 seconds on his treadmill test performed 1 month later. No further worsening occurs over the next 2 years.

Example 5

A 60 year old black female who has a history of three myocardial infarctions and resultant severe (NYHA Class IV) congestive heart failure has been hospitalized with four times in the preceding six weeks for acute decompensation despite therapy with maximally tolerated doses of lasix, isosorbide dinitrate, digoxin, and an ACE inhibitor. Her symptoms include edema, dyspnea at rest, 3 pillow orthopnea, marked fatigue and mental confusion. A decision is made to discontinue the digoxin and institute treatment with (3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17β-carboxylic acid, methyl ester. The initial dose of (3β,5β,14β,17β)-14-Amino-3-[(O-2,6-dideoxy-β-D-ribo-hexopyranosyl-(1→4)-O-2,6-dideoxy-β-D-ribo-hexopyranosyl-(1→4)-2,6-dideoxy-β-D-ribo-hexopyranosyl)oxy]androstane-17β-carboxylic acid, methyl ester is 0.5 mg orally administered once a day, but titration to 2 mg three times a day is required over a 2 month period to adequately control her symptoms. At the end of the two month period, her orthopnea, confusion and edema resolve; and she has an improved ability to perform activities of daily living such as dressing herself without dyspnea (NYHA Class III, moderate congestive heart failure). Her ejection fraction also improves from 20 to 35%. She remains stable over the following three months.

Example 6

A recently (2 months) sober 60 year old white male alcoholic, with a 30 year history of cigarette smoking is admitted to the hospital with a three month history of progressively worsening dyspnea on exertion, fatigue, orthopnea, edema and paroxysmal nocturnal dyspnea. He has dyspnea while brushing his teeth. Physical examination reveals a cachectic male in moderate distress with a respiratory rate of 30 per minute, a heart rate or 110 bpm, blood pressure 90/50, an S3 gallop, 2+ pitting edema to the knees, jugular venous distention, hepatomegaly, ascites, bibasilar rales and an enlarged heart. Extensive evaluation provides diagnoses of chronic alcoholic hepatitis, chronic obstructive pulmonary disease, and moderate (NYHA Class III) congestive heart failure due to toxic (alcoholic) cardiomyopathy. Treatment is begun with hydrochlorthiazide, an ACE inhibitor and 14β-amino-3β-[α-(L)-rhamnopyranosyloxy-(1→4)-α-(L)-rhamnopyranosyloxy]-5β-androstane-17β-carboxylic acid, methyl ester at a daily oral dose of 0.25 mg per day. He improves rapidly and is discharged in a week. After a 20 pound weight loss he is able to walk to the mailbox with mild dyspnea (NYHA Class II). His respiratory rate is 20, heart rate 90, the S3 is no longer audible, and the edema and rales resolve. The hepatomegaly persists unchanged, but the ascites is slightly diminished. The ejection fraction increases from 32 to 45% and the heart size decreases.

Example 7

A 70 year old sedentary white female is noted to have an enlarged heart on CXR done prior to elective surgery for a cataract. She denies any history of chest pain, dyspnea or any history of hypertension, diabetes or cardiac disease. Her ECG shows non-specific ST-T wave changes; and standard clinical laboratory evaluations are normal. A treadmill exercise test is terminated due to fatigue without evidence of coronary artery disease. An echocardiogram shows biventricular enlargement, normal valves and an ejection fraction of 30%. She is given a preventative course of 14β-amino-3β-[α-(L)-rhamnopyranosyloxy-(1→4)-2',3'-O-isopropylidene-α-(L)-rhamnopyranosyloxy]-5β- androstane-17β-carboxylic acid, methyl ester at 0.25 mg orally per day. Her ejection fraction increases to 40% and she is asymptomatic at the time of hospitalization for surgery for a second cataract 5 years later.

What is claimed is:

1. A process for introducing an amino group at the 14-position on asteroid nucleus, wherein said amino group is diasteroselectively introduced onto the 14-position of the steroid nucleus via an iodoisocyanate addition comprising the steps of:
    a) adding the iodoisocyanate to the 14–15 position double bond on the steroid nucleus; and
    b) dehalogenation; and
    c) isocyanate conversion to the amine moiety on the 14-position of the steroid nucleus.

2. A process according to claim 1, wherein said iodoisocyanate addition is accomplished using silver cyanate and iodine.

3. A process according to claim 1, wherein said dehalogenation is accomplished using alkyltin hydrides and radical initiators.

4. A process according to claim 3, wherein said alkyltin hydride is tri-n-butyltin hydride and said radical initiator is benzoyl peroxide.

5. A process according to claim 1, wherein the isocyanate conversion to the amine moiety is via aqueous hydrolysis.

6. A process according to claim 5, wherein said hydrolysis is via the addition of hydrochloric acid.

7. A process according to claim 5, wherein said hydrolysis is via the addition of potassium carbonate.

8. A process according to claim 1 wherein adding the iodoisocyanate is at a temperature of from about −30° C. to about 100° C.

9. A process according to claim 1 wherein the iodoisocyanate step has a reaction time of from about 1 to about 6 hours.

10. A process according to claim 5 wherein adding the iodoisocyanate is at a temperature of from about −30° C. to about 100° C.

11. A process according to claim 5 wherein the iodoisocyanate step has a reaction time of from about 1 to about 6 hours.

12. A process for the preparation of an oligosaccharide containing 14-aminosteroid compound according to claim 1, wherein the amino group on the 14-position of the steroid nucleus is diasteroselectively introduced onto the 14-position of the steroid nucleus via an iodoisocyanate addition comprising the steps of:
    a) reacting silver cyanate and iodine at a temperature from about −30° C. to 100° C. for about 1 to about 6 hours to generate iodoisocyanate to the 14–15 position double bond on the steroid nucleus; and
    b) dehalogenating at a temperature from about 0° C. to about 100° C. for about 1 to about 6 hours; and
    c) hydrolyzing the isocyanate group to the amine moiety on the 14-position of the steroid nucleus at a temperature from about 0° C. to about 60° C. for about 2 to about 72 hours.

* * * * *

UNITED STATES PATENT AND TRADEMARK OFFICE
CERTIFICATE OF CORRECTION

PATENT NO. : 5,710,259

DATED : January 20, 1998

INVENTOR(S) : Paul Michael Dybas; Roland Norman Johnson; Randy Stuart Muth: Song Liu.

It is certified that error appears in the above-identified patent and that said Letters Patent is hereby corrected as shown below:

Column 67, line 7, "asteroid", should read -- a steroid --

Column 67, line 8, "diasteroselectively", should read -- diastereoselectively --

Column 68, line 16, "diasteroselectively", should read -- diastereoselectively --

Signed and Sealed this

Fifth Day of May, 1998

Attest:

BRUCE LEHMAN

Attesting Officer

Commissioner of Patents and Trademarks